United States Patent
Bonnette et al.

(10) Patent No.: US 6,875,193 B1
(45) Date of Patent: Apr. 5, 2005

(54) RAPID EXCHANGE FLUID JET THROMBECTOMY DEVICE AND METHOD

(75) Inventors: Michael John Bonnette, Minneapolis, MN (US); Eric Joel Thor, Arden Hills, MN (US); Stephen Earl Weisel, Montrose, MN (US); Amanda J. Wong, Minneapolis, MN (US)

(73) Assignee: Possis Medical, Inc., Minneapolis, MN (US)

( * ) Notice: Subject to any disclaimer, the term of this patent is extended or adjusted under 35 U.S.C. 154(b) by 252 days.

(21) Appl. No.: 10/198,264

(22) Filed: Jul. 16, 2002

Related U.S. Application Data

(60) Continuation-in-part of application No. 09/888,455, filed on Jun. 25, 2001, now Pat. No. 6,755,803, which is a continuation-in-part of application No. 09/356,783, filed on Jul. 16, 1999, now abandoned, which is a division of application No. 09/019,728, filed on Feb. 6, 1998, now Pat. No. 5,989,210.

(51) Int. Cl.[7] .............................................. A61B 17/20
(52) U.S. Cl. ............................. 604/22; 604/35; 604/43; 604/93.01; 604/131; 604/164.01; 604/164.13; 604/533; 606/41; 606/127; 606/159
(58) Field of Search .............................. 604/164.01, 19, 604/22, 27, 35, 43, 93.01, 118–120, 131, 151, 164.13, 166.01, 173, 246, 257, 264, 523, 529, 532–535, 538, 284, 317; 606/41, 107, 127, 159

(56) References Cited

U.S. PATENT DOCUMENTS

| | | | |
|---|---|---|---|
| 5,370,609 A | * 12/1994 | Drasler et al. | ................. 604/22 |
| 5,571,094 A | * 11/1996 | Sirhan | .......................... 604/284 |
| 5,683,345 A | * 11/1997 | Waksman et al. | ............... 600/3 |
| 5,713,849 A | * 2/1998 | Bosma et al. | .................. 604/28 |
| 6,001,078 A | * 12/1999 | Reekers | ........................ 604/43 |
| 6,592,549 B2 | * 7/2003 | Gerdts et al. | ........... 604/103.04 |

* cited by examiner

*Primary Examiner*—Nicholas D. Lucchesi
*Assistant Examiner*—Jennifer J Maynard
(74) *Attorney, Agent, or Firm*—Hugh D. Jaeger

(57) ABSTRACT

A rapid exchange fluid jet thrombectomy device for removal of thrombus or unwanted tissue debris from a vein, artery or the like. The device includes a semi-rigid intermediate tube between a proximal and a distal exhaust tube which accommodates a guidewire tube exit located along the catheter at less than one-half the length of the catheter measured from the catheter most distal point. Such a location of the guidewire is convenient for maneuvering and longitudinal advancement of the guidewire, as well as maneuvering and longitudinal advancement of the catheter by one practitioner.

15 Claims, 19 Drawing Sheets

RAPID EXCHANGE FLUID JET THROMBECTOMY DEVICE AND METHOD

CROSS REFERENCES TO RELATED APPLICATIONS

This patent application is a continuation-in-part of Ser. No. 09/888,455 entitled "Single Operator Exchange Fluid Jet Thrombectomy Device" filed on Jun. 25, 2001, now U.S. Pat. No. 6,755,803, which is a continuation-in-part of Ser. No. 09/356,783 entitled "Rheolytic Thrombectomy Catheter and Method of Using Same" filed on Jul. 16, 1999, now abandon, which is a divisional of Ser. No. 09/019,728 entitled "Rheolytic Thrombectomy Catheter and Method of Using Same" filed on Feb. 6, 1998, now U.S. Pat. No. 5,989,210.

This patent application is also related to Ser. No. 09/417,395 entitled "Thrombectomy Catheter and System" (as amended) filed on Oct. 13, 1999, pending, which is a continuation-in-part of Ser. No. 08/349,665 entitled "Thrombectomy Method" filed on Dec. 5, 1994, under appeal, which is a divisional of Ser. No. 08/006,076 entitled "Thrombectomy Device" filed on Jan. 15, 1993, now U.S. Pat. No. 5,370,609, which is a continuation of Ser. No. 07/563,313 entitled "Thrombectomy Device and Method" filed on Aug. 6, 1990, abandoned.

This patent application is also related to Ser. No. 08/351,605 entitled "Thrombectomy and Tissue Removal Method and Device" filed on Dec. 8, 1994, pending, which is a divisional of Ser. No. 07/976,367 entitled "Thrombectomy and Tissue Removal Method and Device" filed on Nov. 13, 1992, abandoned, which is a continuation-in-part of Ser. No. 07/563,313 entitled "Thrombectomy Device and Method" filed on August 06, 1990, abandoned.

BACKGROUND OF THE INVENTION

1. Field of the Invention

The present invention relates to a rapid exchange catheter, such as a fluid jet material removal catheter and system, to a method of constructing same, and to a method of using same in diagnosis or treatment of a body vessel or other body cavity or tissue.

The present invention relates to apparatus for use in treatment of the human body. More particularly, the present invention relates to an elongated device which may be a single catheter assembly or a multiple component catheter assembly and which is suitable for use through percutaneous or other access, for endoscopic procedures, or for intraoperative use in either open or limited access surgical procedures. Still more particularly, the present invention relates to an elongated device in the form of a fluid jet thrombectomy catheter, being adapted for fragmentation and removal of thrombus or other unwanted material from blood vessels or body cavities by using high velocity saline (or other suitable fluid) jets to macerate the thrombus or other unwanted material. The elongated device bears certain similarities to known waterjet thrombectomy catheter devices and can be used as such, but differs therefrom in several material respects, with major differences being the construction of the device from simpler tubular components, utilization of a semi-rigid intermediate tube to facilitate transition between a guidewire-containing and a non-guidewire-containing portion, and enhanced utility of the device in rapid exchange methods with a single operator. The device is particularly advantageous in a cross stream configuration but can be adapted to other forms as well. The cross stream jets create a recirculation flow pattern optimized for clearing a large cross section of mural thrombus or other similar material. Further, the present invention also relates to a system constituted either by the combination of the elongated device with both pressurized fluid source means and exhaust regulation means or by the combination of the elongated device with only pressurized fluid source means. Other ancillary devices or features can be utilized or incorporated such as introduction devices, guiding devices, isolation or filtering devices, centering devices, imaging devices, infusion or withdrawal devices, dilatation devices, energy delivery devices, and so forth, to aid in diagnosis or treatment of a patient, without departing from the scope of the present invention. The use of a semi-rigid intermediate tube can be applied to other elongated devices such as intravascular catheters, balloon catheters, device delivery catheters, and so forth, and is not limited solely to fluid jet material removal catheters.

2. Description of the Prior Art

Procedures and apparatus have been developed for ease in removing tissue and various deposits. Several such devices employ a jet of saline as the working tool to help break up the tissue deposit and further provide a suction means to remove the deposit. U.S. Pat. No. 5,135,482 to Neracher describes a hydrodynamic device for removal of organic deposit from a human vessel. A supply of saline is delivered by a high pressure duct to the distal end of a catheter. The saline exits the duct as a jet that is directed generally forward and directly toward the tissue to be broken up. The duct is contained within and can move axially with respect to a hose that is positioned around the duct. A vacuum suction is applied to the hose to remove the debris that is created from the broken-up tissue. There is no guidewire lumen and no provision for rapid exchange of the device over a guidewire.

Another drainage catheter, described by Griep in U.S. Pat. No. 5,320,599, has a discharge channel and a pressure channel. The channels are formed into a single catheter tube such that the two tubes are fixed with respect to each other. This device does not have a guidewire lumen and cannot be used as a rapid-exchange wire-guided device.

Waterjet thrombectomy catheters have been described (including U.S. Pat. Nos. 5,370,609, 5,989,210, 6,096,001 and 6,224,570) in which a distal-to-proximal directed waterjet(s) flow(s) past a window, orifice or gap at the distal end of the catheter, re-entering the catheter and pushing flow through an evacuation lumen. When placed in a vessel containing thrombus and activated, the high velocity jet(s) will entrain surrounding fluid and thrombus into the window, orifice or gap region, where the high shear forces of the jet(s) will macerate the thrombus. The macerated particles will be removed from the body by the pressure generated on the distal end of the evacuation lumen by the impingement of the high velocity waterjet(s).

A limitation of these waterjet thrombectomy catheters has been the inability to remove organized, wall-adherent thrombus from large vessels. In accordance with the present invention, the rapid exchange fluid jet thrombectomy device described overcomes this limitation by utilizing cross stream jets to optimize the recirculation pattern at the tip of the device and increase the drag force exerted on the mural thrombus to break it free from the vessel wall and allow it to be removed by the device.

Prior art devices often required the use of more than one operator where one operator must stabilize the guidewire while the second operator introduces the catheter over the guidewire into the anatomy. Various approaches have been used to overcome this difficulty, with varying degrees of success. Bonzel U.S. Pat. No. 4,762,129, Yock U.S. Pat. No. 5,040,548, Keith U.S. Pat. No. 5,156,594, Keith et al. U.S. Pat. No. 5,370,616, Horzewski et al. U.S. Pat. No. 5,496,346, Enger U.S. Pat. No. 5,728,067, and Enger U.S. Pat. No. 5,980,486 disclose balloon catheters which include a short guidewire lumen near the distal end, to provide for rapid or single-operator exchange. The Bonzel patent discloses a balloon catheter which has a short guidewire lumen only passing through a distal balloon and alongside a balloon inflation lumen which terminates in the balloon; this approach is not appropriate for a cross stream type fluid jet catheter where internal pressure would cause a significant leakage from the exhaust lumen through the proximal opening of the guidewire lumen and into the vessel, and a side-by-side asymmetric configuration would cause the guidewire or guidewire lumen to interfere with access of the jets or the cross stream jets to the thrombus and would be stiffer, thereby not being able to track as well. The Yock patent discloses a balloon catheter with a guidewire lumen which extends some distance proximal to the balloon, with the proximal and distal inflation lumens and guidewire lumen being preferably of flexible plastic material; the Yock device lacks a semi-rigid intermediate tube which provides reliable geometry to ensure free guidewire movement in this region, and provides a more efficient yet controllable fabrication. As with the Bonzel and Yock devices, the Keith et al., Horzewski et al., and Enger devices are balloon catheters not adapted for fluid jet thrombectomy. The present invention provides a high-pressure supply lumen to supply the fluid jets, and an exhaust lumen for removal of thrombus or unwanted tissue debris, both extending along the length of the device, in addition to a shorter guidewire lumen extending only a portion of the length of the device. None of the prior art devices provides these three lumens to provide the form or function of the present invention.

Co-pending application Ser. No. 09/888,455, assigned to the same assignee as the present invention, discloses a fluid jet thrombectomy catheter which is adapted for single operator exchange. That device provides an interchangeable system where one inner catheter assembly containing fluid jet orifices can be substituted for a different inner catheter assembly according to the particular requirements of the material removal procedure in the vasculature. However, that device requires two separate components, resulting in compatibility and alignment issues necessitating more complex designs with alignment stops and more expensive fabrication than the present design, and requires additional manipulations by the physician to utilize the device. When such interchangeable inner catheter assemblies are not required, the present invention provides a simpler unitary device with more straightforward operation.

The present invention overcomes complexities of the prior art by introducing a semi-rigid intermediate tube which connects a distal exhaust tube, a guidewire lumen, and a proximal exhaust tube in an efficient and easily fabricated configuration, and provides reliable operation over a guidewire and which is applicable for removal of unwanted deposits in the body, such as, but not limited to, thrombus in a blood vessel or cardiac chamber or extravascular space, renal or biliary deposits, hematomas in the brain or brain ventricles or elsewhere, material in the gastrointestinal tract, material in the respiratory tract or lungs, or material associated with a joint, for example. The present invention is particularly useful in a fluid jet thrombectomy device.

The present invention also includes a rapid exchange fluid jet system, and a semi-rigid intermediate tube, and a method of fabricating a multiple-lumen rapid exchange catheter, and a method of removing unwanted tissue from the body using a rapid exchange fluid jet catheter and system.

SUMMARY OF THE INVENTION

The present invention, a rapid exchange fluid jet thrombectomy device, is a medical device for removal of material such as thrombus from a vessel or other body cavity. As shown in one or more embodiments, the rapid exchange fluid jet thrombectomy device can function as a rheolytic thrombectomy catheter for removing tissue from a vessel or other body cavity.

A catheter according to the present invention has a high pressure lumen which carries pressurized working fluid such as saline solution from the proximal end to the distal end which has a jet emanator, where the working fluid exits to form one or more high velocity fluid jets. The jet(s) can be directed proximally, distally, with radial componency, or various directions; the jet(s) directed proximally are preferred. When the high velocity jets are operating, blood, thrombus, or other fluid or unwanted material is drawn in through inflow orifice(s) or other openings into a distal exhaust tube due to a low pressure zone created by the high velocity jets. Further, proximal to this low pressure zone, the distal exhaust tube thereby becomes somewhat pressurized, with the pressure being able to drive fluid and unwanted material proximally along the exhaust tube. Preferably, there is one or more outflow orifice(s) in the pressurized region of the distal exhaust tube, so that a portion of the fluid and unwanted material (which has been broken into small pieces by the high velocity jets) passes out from the distal exhaust tube into the body vessel or cavity in which the catheter has been placed, creating one or more "cross stream" jet(s) with radial componency. These cross stream jets act to break unwanted material off the surface of the body vessel or cavity and aid in creating a fluid recirculation pattern for more effective removal of unwanted material. The basic design of the rapid exchange fluid jet catheter could function without separate outflow orifice(s), but these outflow orifices being separate from inflow orifice(s) or openings provides a more efficient and effective removal of unwanted material. A separate guidewire tube inside the distal exhaust tube provides for passage of a guidewire through the most distal tip of the distal exhaust tube and out the proximal end of the distal exhaust tube. The distal end of the catheter may preferably be tapered to better approximate the diameter of the guidewire and provide better passage within the body vessel or cavity or past a tight stenosis or lesion. The proximal portion of the rapid exchange fluid jet catheter has a proximal exhaust tube but does not contain a guidewire lumen. At the proximal end of the catheter, there is a manifold which includes a high pressure connector and an exhaust connector or, alternatively, can be a continuous line from a waste bag to the exhaust tube or to the pump. The distal exhaust tube typically extends less than half the length of the catheter, and the proximal exhaust tube typically extends greater than half the length of the catheter.

Interposed between the proximal exhaust tube and the distal exhaust tube is a relatively short semi-rigid intermediate tube. The intermediate tube is round at its proximal end to fit snugly inside the distal end of the proximal exhaust tube. The intermediate tube is formed or otherwise constructed to have a truncated and rounded slot which is shallower towards the proximal end and deeper toward the distal end. This truncated and rounded slot is sized so that the guidewire tube will fit inside the truncated and rounded slot at the distal end, and the intermediate tube is formed so that it fits snugly inside the proximal end of the distal exhaust tube. The proximal end of the guidewire tube is located along the truncated and rounded slot of the semi-rigid intermediate tube, and preferably near the proximal end of the distal exhaust tube. The guidewire tube is positioned and sized so that a guidewire can pass through the distal end of the guidewire tube located at or near the distal tapered end of the catheter, through the length of the distal exhaust tube, and then exit through the proximal end of the distal exhaust tube located near the proximal end of the intermediate tube. The high pressure lumen connects to the high pressure connector or can run all the way to a pump at the proximal manifold, and passes within the proximal exhaust tube, the intermediate tube, and the distal exhaust tube. Adhesive sealant may be used to bond the various components to provide a fluid seal between components. Alternatively, thermal bonding or heat-shrinking can be used, or the components may be sized to form a tight, secure fit without additional bonding.

The present invention also includes a design of an intermediate tube for a rapid exchange catheter, which may be a fluid jet catheter, a balloon catheter, or other diagnostic or treatment catheter.

The present invention also includes a rapid exchange fluid jet catheter system incorporating a rapid exchange fluid jet catheter, a high pressure fluid source, and a collection system with optional exhaust regulation means, where a guidewire passes through only the distal portion of the rapid exchange fluid jet catheter.

The present invention also includes a method of fabricating such a rapid exchange catheter utilizing a semi-rigid intermediate tube. The method includes the steps of:
 a. providing a proximal exhaust tube, a distal exhaust tube, a guidewire tube, and a semi-rigid intermediate tube with a truncated and rounded slot which is deeper at the distal end than at the proximal end;
 b. fitting the proximal exhaust tube to the proximal end of the semi-rigid intermediate tube and fitting the distal exhaust tube to the distal end of the semi-rigid intermediate tube; and,
 c. positioning the guidewire tube so that it extends along the length of the distal exhaust tube and terminates at or near the distal end of the distal exhaust tube, and extends proximally to a point along the truncated and rounded slot of the semi-rigid intermediate tube, thereby providing communication for passage from the outside of the rapid exchange catheter at the distal end of the guidewire tube located at or near the distal tapered end of the catheter, through the length of the distal exhaust tube, i.e., through the guidewire tube, and then exiting through the proximal end of the distal exhaust tube at a location near the proximal end of the semi-rigid intermediate tube.

The above embodiment of the present invention also provides a method of removing thrombus or other unwanted material from a body vessel or cavity. The method includes the steps of:
 a. providing a guidewire and rapid exchange fluid jet catheter including a manifold, a proximal exhaust tube, a distal exhaust tube, a semi-rigid intermediate tube, a guidewire tube, a high pressure lumen, a proximal high pressure connector, and a distal jet emanator;
 b. advancing the guidewire through the vasculature and past the vascular site containing thrombus or other unwanted material;
 c. introducing the rapid exchange fluid jet catheter by passing the guidewire through the guidewire tube and advancing the rapid exchange fluid jet catheter along the guidewire to the site containing thrombus or other unwanted material; and,
 d. providing a high pressure supply of saline or other fluid to the high pressure lumen via the proximal high pressure connector or direct connection to a pump, so as to cause at least one high velocity fluid jet to emanate from the jet emanator and to entrain thrombus or other unwanted material into the distal exhaust tube via an inflow orifice where the thrombus or other unwanted material is macerated and propelled proximally along the distal exhaust tube, semi-rigid intermediate tube, and proximal exhaust tube for removal from the body, while either maintaining a positive or negative fluid balance at the distal tip.

The method of removing thrombus or other unwanted material from a body vessel or cavity preferably includes providing a distal exhaust tube with outflow orifices, which create cross stream jets for enhanced removal of material.

According to one or more embodiments of the present invention, there is provided a rapid exchange fluid jet thrombectomy device, including a manifold including connector and other devices, a proximal exhaust tube extending distally from the manifold, a semi-rigid intermediate tube extending distally from the proximal exhaust tube, a truncated and rounded slot extending along a greater portion of the semi-rigid intermediate tube, a distal exhaust tube extending distally from the semi-rigid intermediate tube, an accessible guidewire tube accommodated by and extending along and from a portion of the truncated and rounded slot into and along the greater portion of the distal exhaust tube, a fluid jet emanator connected to a high pressure tube extending through the distal exhaust tube, the semi-rigid intermediate tube, and the proximal exhaust tube, and a plurality of inflow and outflow orifices located at the distal end of the distal exhaust tube. One or more alternative embodiments disclose a distal exhaust tube incorporating a bi-directional fluid jet emanator which emanates high velocity jet flow in a distal direction from a plurality of distally facing jet orifices for breakup and macerating of thrombotic deposits or lesions in coordination with pluralities of outflow orifices and inflow orifices, and which also emanates high velocity jet flow in a proximal direction from a proximally facing orifice in coordination with an inflow orifice to carry off macerated thrombotic deposits or lesions outwardly through the lumen of a distal exhaust tube.

One significant aspect and feature of the present invention is a rapid exchange fluid jet thrombectomy device which can be operated by one practitioner.

Another significant aspect and feature of the present invention is a rapid exchange fluid jet thrombectomy device having inflow orifices and outflow orifices to create cross stream jets.

Still another significant aspect and feature of the present invention is a guidewire tube for passage of a guidewire through the distal portion of the device.

Yet another significant aspect and feature of the present invention is a semi-rigid intermediate tube to provide connection between a proximal exhaust tube, a distal exhaust tube, and a guidewire tube.

A further significant aspect and feature of the present invention is an easier method of utilizing a fluid jet catheter due to a unitary design.

A still further significant aspect and feature of the present invention is the ability to incorporate various emanator shapes, styles and designs.

An additional significant aspect and feature of the present invention is the reduction of fabrication costs by eliminating complicated extruded shapes, minimizing the number of components, reducing the complexity of the components, and improving the quality of the components.

Another significant aspect and feature of the present invention is the inclusion of structural members which allow minimizing the outer diameter of the device while maximizing the inner diameter of the device. The outer diameter of the device is minimized to provide the least intrusive profile and the inside diameter of the device is maximized for higher free and less restrictive exhaust flow.

A yet further significant aspect and feature of the present invention is coating the device hydrophilically for improved movement along a guidewire, as well as improved trackability.

Another significant aspect and feature of the present invention is the incorporation of an exhaust tube support ring and of the structure of a fluid jet emanator in conjunction with marker bands to provide for stabilization of the inflow and outflow orifices when passed through tortuous vascular paths, as well as the ability to be suitably detected by fluoroscopic identifying measurement devices.

Another significant aspect and feature of the present invention is the ability to inject medicinal or detectable fluids into the body through the exhaust port of a manifold.

Another significant aspect and feature of the present invention is the ability to inject drugs through emanator jets via a saline supply bag.

Alternatively, another significant aspect and feature of the present invention is the use of a bi-directional fluid jet emanator for directing high velocity jet flows in both distal and proximal directions.

Alternatively, another significant aspect and feature of the present invention is the use of a dedicated set of inflow and outflow orifices and dedicated jet orifices for use in the breakup and maceration and re-maceration of lesions and thrombotic material.

Alternatively, another significant aspect and feature of the present invention is the use of a dedicated inflow orifice and dedicated jet orifice for use in the evacuation of macerated and re-macerated particles of lesions and thrombotic material through a distal exhaust tube.

Having thus described embodiments and significant aspects and features of the present invention, it is the principal object of the present invention to provide a rapid exchange fluid jet thrombectomy device and method of using same to remove thrombus or other unwanted material from a body vessel or other body cavity.

One object of the present invention is to provide a rapid exchange fluid jet thrombectomy device of such size, flexibility and construction as to enable it to pass readily through the tortuous pathways found in the fragile vessels of the heart, the brain or other body areas, including the more fragile veins.

Another object of the present invention is to provide a rapid exchange fluid jet thrombectomy device with means for producing one or more jets of saline and projecting them in a proximal direction to create a vacuum near the site of thrombus or other unwanted material while pressurizing the exhaust passage.

Yet another object of the present invention is to provide a rapid exchange fluid jet thrombectomy device with outflow orifice means for producing one or more cross stream jets for enhanced removal of thrombus or other unwanted material.

Still another object of the present invention is to provide an improved method of removing thrombus or other unwanted material from an obstructed body vessel.

A further object of the present invention is to provide a smaller diameter rapid exchange fluid jet thrombectomy device wherein the guidewire passes through only a portion of the device resulting in less pressure drop along the exhaust passage, which can also improve the flow of dye through the guide catheter, thereby increasing catheter performance and procedural performances.

A still further object of the present invention is to provide an efficient, reliable, and less costly method of fabricating a rapid exchange catheter by utilizing a semi-rigid intermediate tube formed with a truncated and rounded slot.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
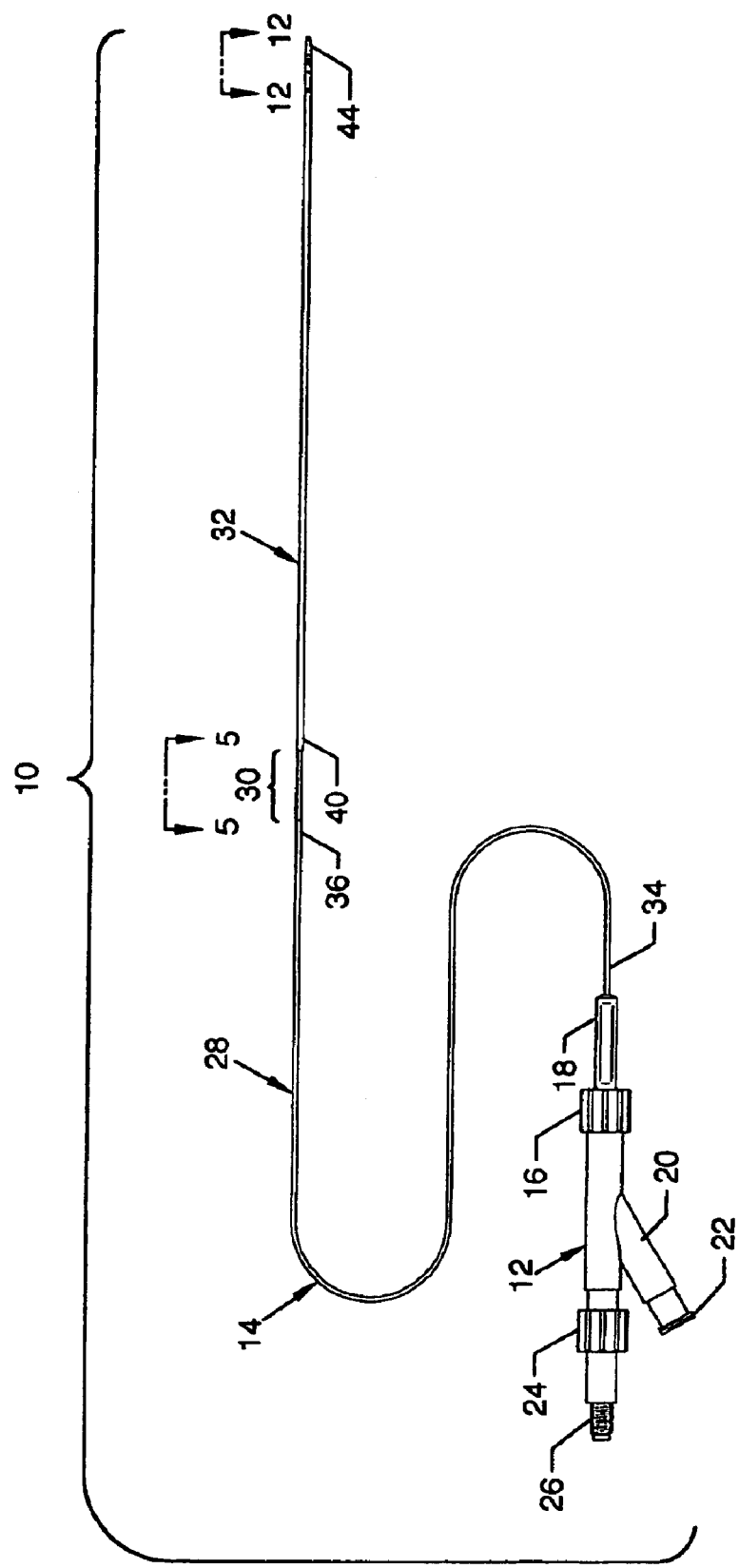
FIG. 1 illustrates a plan view of the visible components of a rapid exchange fluid jet thrombectomy device, the present invention, including a manifold with a strain relief and a catheter extending distally from the strain relief.

FIG. 1 illustrates a plan view of the visible components of a rapid exchange fluid jet thrombectomy device 10, the present invention, including a manifold 12 and a catheter 14. The manifold 12 includes a distally located Luer fitting 16 and strain relief 18, an exhaust branch 20 and threaded branch end 22, a proximally located Luer fitting 24, and threaded high pressure connection port 26. The catheter 14, a unitary elongated structure, extends distally from the strain relief 18 and includes multiple components comprising, but not limited to, a one-piece proximal exhaust tube 28, a one-piece semi-rigid intermediate tube 30, and a one-piece distal exhaust tube 32 connected in series fashion, a guidewire tube 46 (FIG. 3), and other features and components as described herein. The proximal exhaust tube 28 and the distal exhaust tube 32 are fashioned of braided polyimide to provide for minimal wall thickness for improved free exhaust and dye flow characteristics, while still maintaining pushability through the vasculature, but still maintaining not overly stiff properties.

The proximal end 34 of the one-piece proximal exhaust tube 28 secures to the manifold 12 by the use of the Luer fitting 16 and extends distally through the strain relief 18 to a location where the distal end 36 terminates around and about the proximally located tubular portion 38 (FIG. 3) of the semi-rigid intermediate tube 30. The proximal end 40 of the one-piece distal exhaust tube 32 aligns over and about part of the distally located tubular portion 42 (FIG. 3) of the semi-rigid intermediate tube 30 and extends distally to a tapered tip 44 which can be flexible in design.

Figure 2:
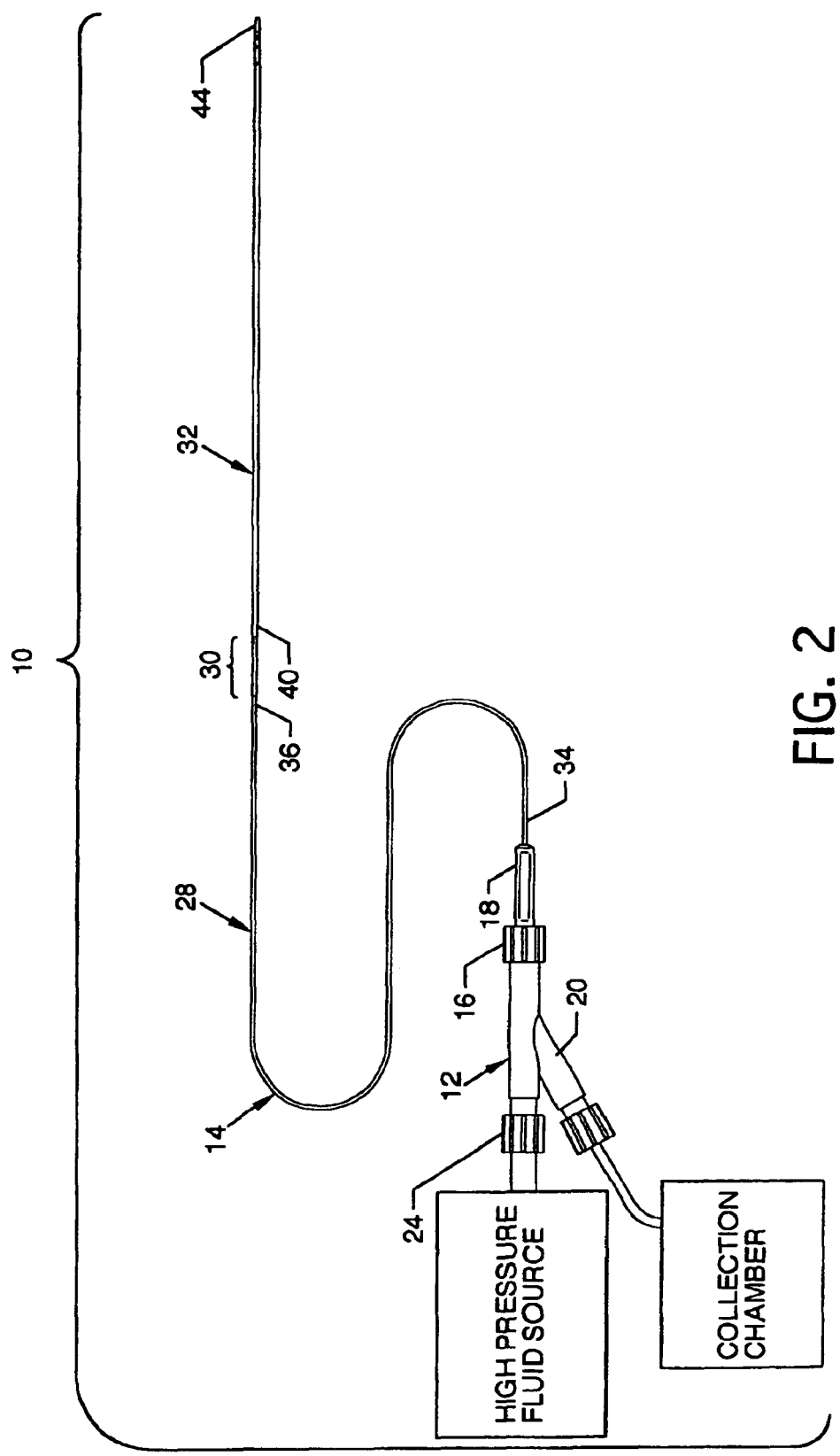
FIG. 2 illustrates a plan view of the rapid exchange fluid jet thrombectomy device, the present invention, indicating high pressure fluid source and collection chamber connections to the manifold.

FIG. 2 illustrates a plan view of the rapid exchange fluid jet thrombectomy device 10, the present invention, indicating high pressure fluid source and collection chamber connections to the manifold 12.

Figure 3:
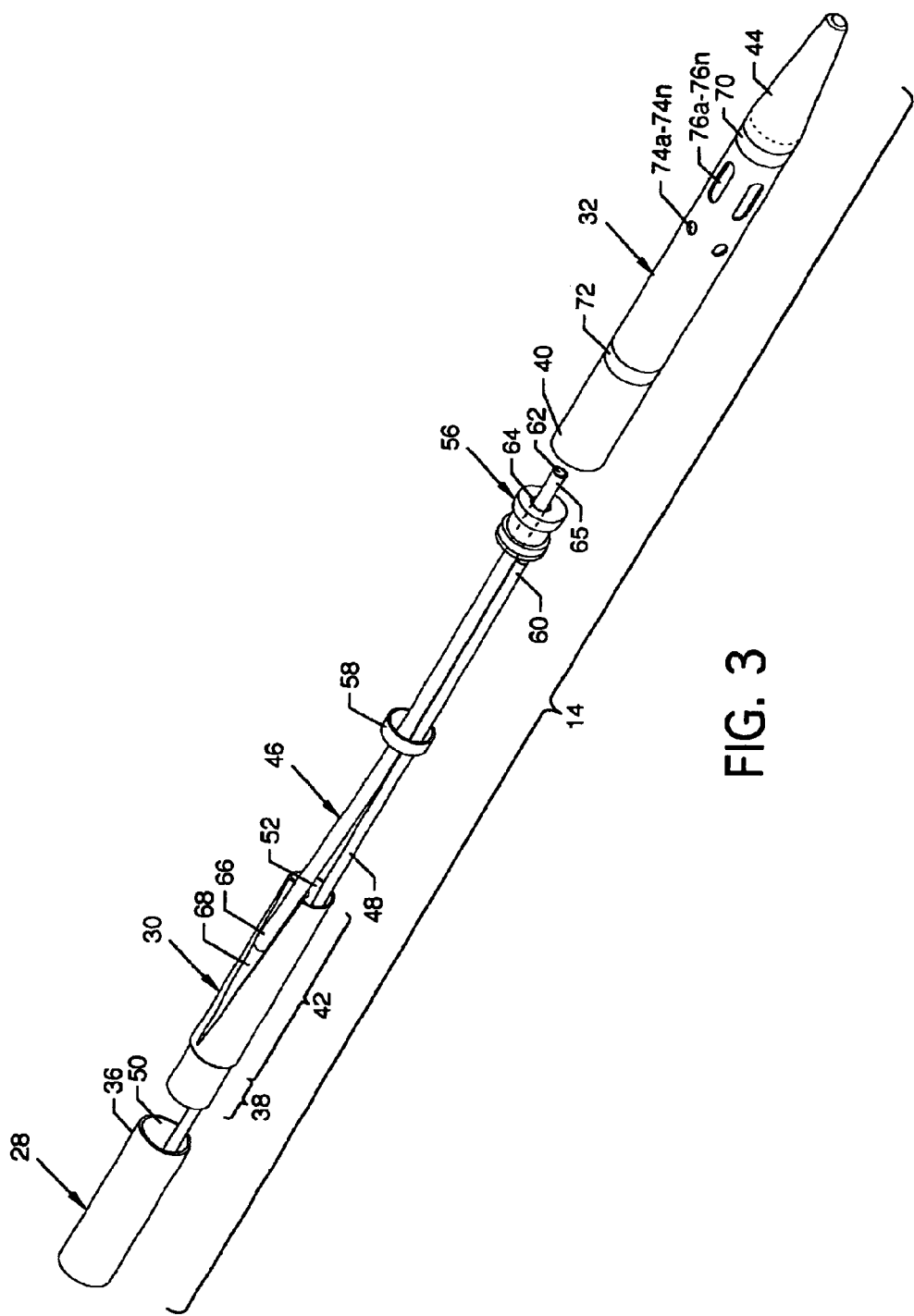
FIG. 3 illustrates an exploded and foreshortened isometric view of the components of the catheter of the rapid exchange fluid jet thrombectomy device distal to the strain relief.

FIG. 3 illustrates an exploded isometric view of the components of catheter 14 distal to the strain relief 18, the components being foreshortened with respect to length for the purpose of illustration and clarity. The outwardly visible length of the catheter 14 is comprised of outwardly visible joined components including the proximal exhaust tube 28, the semi-rigid intermediate tube 30, the distal exhaust tube 32, and a small portion of a guidewire tube 46. Other components are housed within, around and about the catheter 14.

Figure 12:
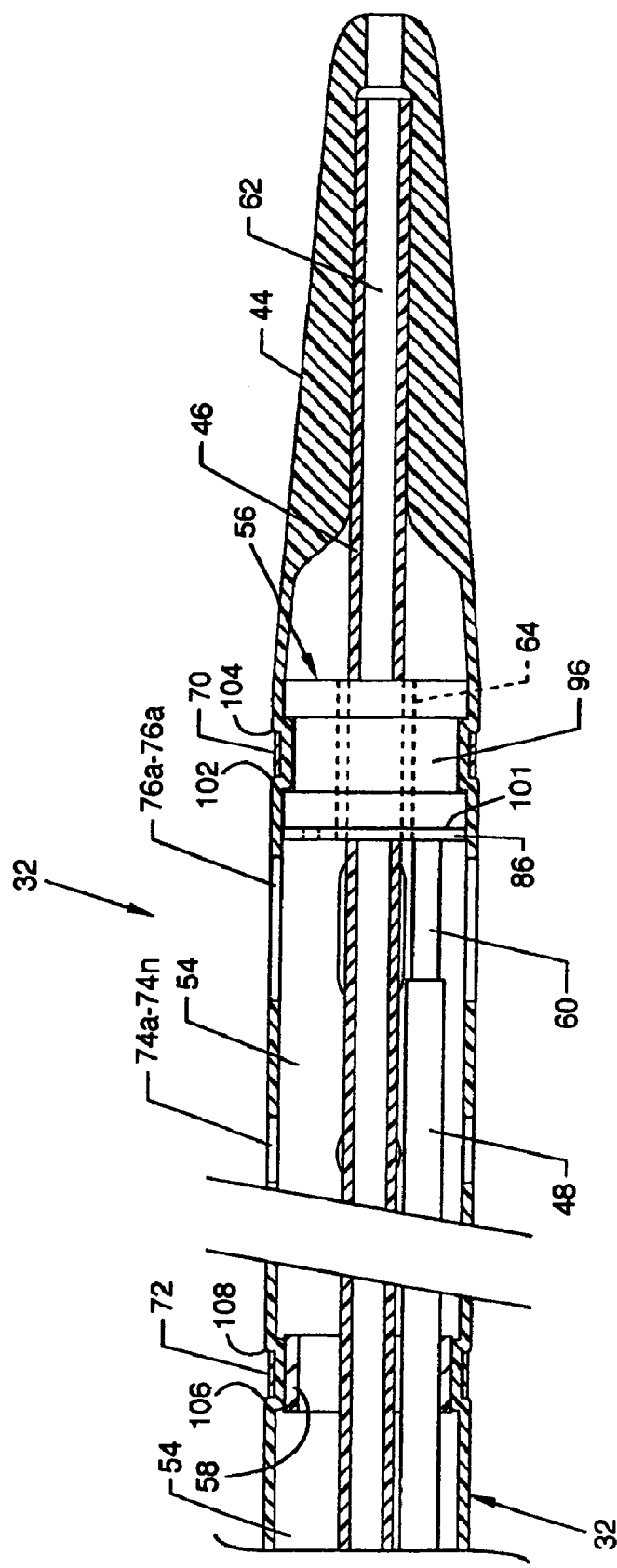
FIG. 12 illustrates a cross sectional view of the distal portion of the distal exhaust tube along line 12—12 of FIG. 1.

A high pressure tube 48 with a lumen 78 (FIG. 5) extends from the manifold 12 as previously described through a lumen 50 in the proximal exhaust tube 28, through a lumen 52 in the semi-rigid intermediate tube 30, and through a lumen 54 (FIG. 12) of the distal exhaust tube 32 and connectively terminates at a fluid jet emanator 56. The high pressure tube 48 also extends through and is attached to an exhaust tube support ring 58 such as by welding or other suitable means. The fluid jet emanator 56 as well as the distal end 60 of the high pressure tube 48 locate distally in the lumen 54 of the distal exhaust tube 32, as shown in FIG. 12. A radiopaque marker band 70 aligns over and about the distal region of the distal exhaust tube 32 and is forcibly secured thereto in captured alignment and in transmitted frictional engagement with the fluid jet emanator 56, as shown in FIG. 12. The exhaust tube support ring 58 locates in lumen 54 of the distal exhaust tube 32 in alignment with a radiopaque marker band 72 which forcibly secures over and about the distal exhaust tube 32 in transmitted frictional engagement, as shown in FIG. 12. The guidewire tube 46, having a lumen 62, extends distally from the semi-rigid intermediate tube 30, through the exhaust tube support ring 58, through a passageway 64 in the fluid jet emanator 56, through the lumen 54 of the distal exhaust tube 32 where the distal end 65 terminates securely at the distal end of the tapered tip 44. Heat can be applied to form a tapered tip 44 of increasingly flexible shape, in a distal direction, at the end of the distal exhaust tube 32, as well as to engagingly secure the distal end of the guidewire tube 46 centrally within the tapered tip 44. The tapered tip 44 may also be formed through a cold draw down process or may be physically attached through adhesives or polymer reintegration. The tapered tip 44 and the guidewire tube 46 are continuous. The proximal end 66 of the guidewire tube 46 is securely accommodated by a truncated and rounded slot 68 of the semi-rigid intermediate tube 30 described with reference to FIG. 4. A plurality of outflow orifices 74a–74n and a plurality of inflow orifices 76a–76n spaced distal to the outflow orifices 74a–74n are included around and about the distal region of the distal exhaust tube 32.

Figure 4:
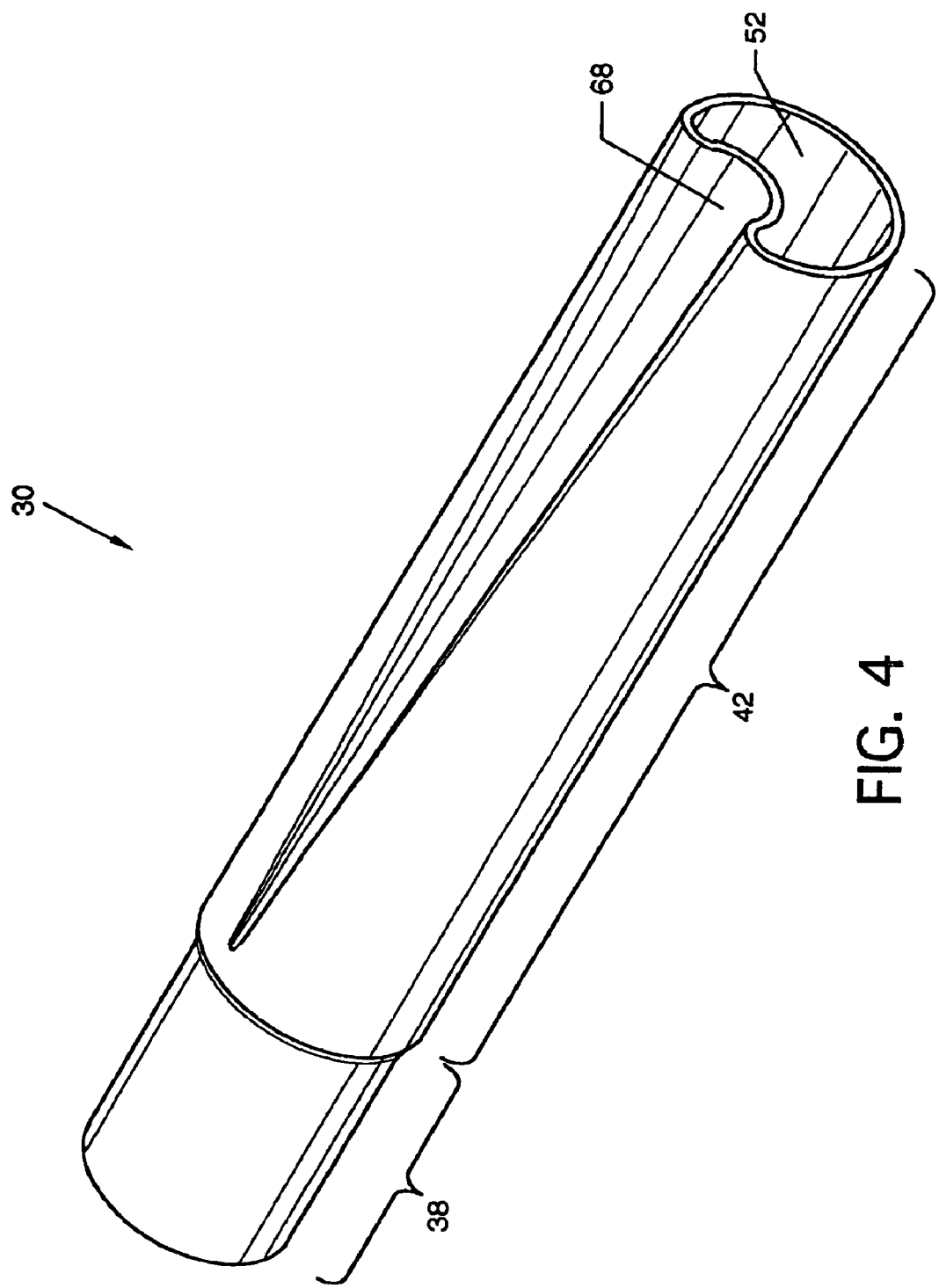
FIG. 4 illustrates an isometric view of the one-piece semi-rigid intermediate tube.

FIG. 4 illustrates an isometric view of the one-piece semi-rigid intermediate tube 30, which could alternatively be rigid, and which can be formed, molded, machined, extruded or otherwise fashioned of metal, plastic or other suitable materials. The one-piece semi-rigid intermediate tube 30 includes a proximally located tubular portion 38 of lesser diameter than the greater length distally located tubular portion 42. The semi-rigid intermediate tube 30 includes geometry in the form of a truncated and rounded slot 68 of decreasing depth, in a proximal direction, which accommodates a guidewire tube 46 (FIG. 5) extending along a greater portion of the length of the distally located tubular portion 42. The truncated and rounded slot 68 is substantially formed in the shape of a nearly full semi-circular arc at the extreme distal end of the distally located tubular portion 42. The arc, while the radius remains constant, is decreased progressing proximally from the extreme distal end of the distally located tubular portion 42 to provide for angled transitional accommodation of the guidewire tube 46 shown in FIG. 5. Lumen 52 interior to the semi-rigid intermediate tube 30 accommodates the high pressure tube 48 and also functions as part of the overall effluent exhaust path formed with lumens 50 and 54.

Figure 5:
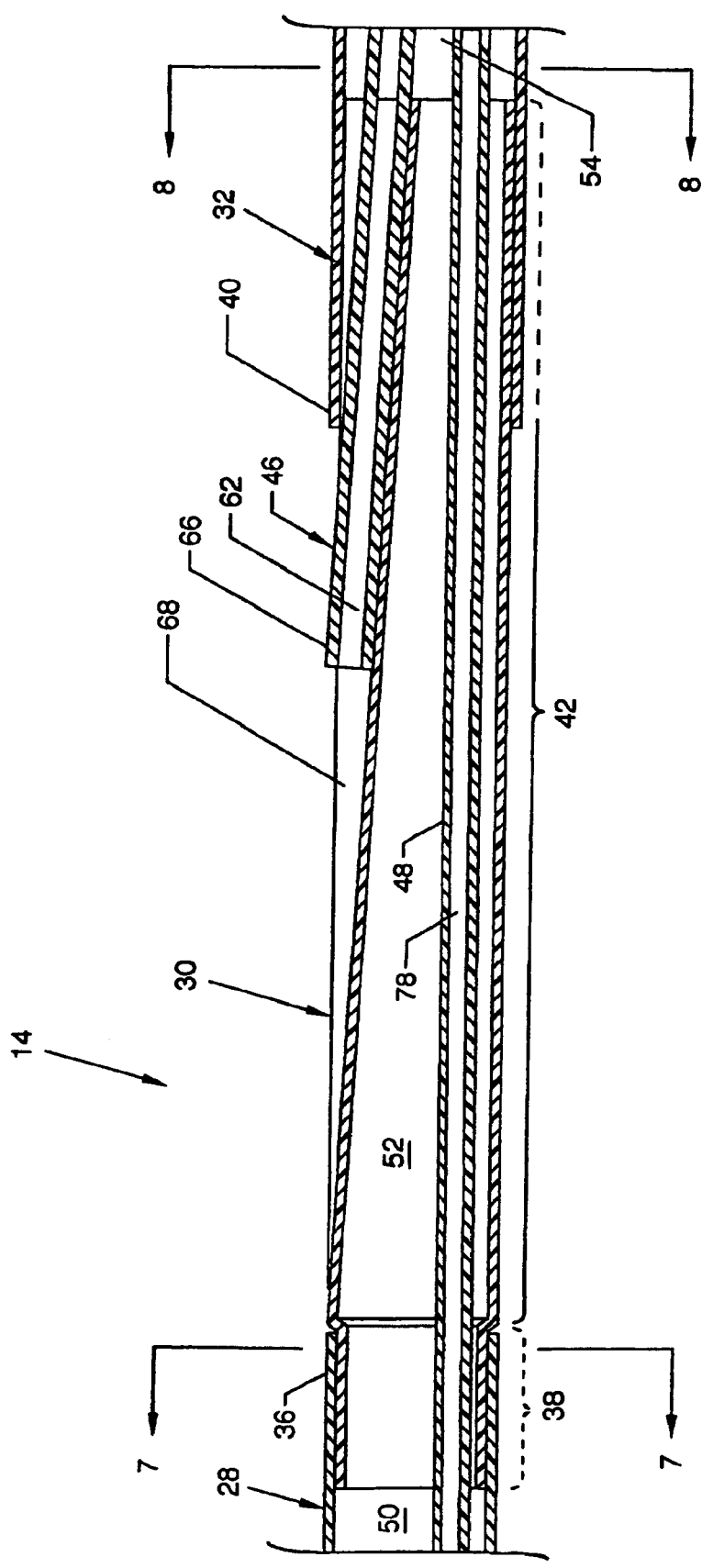
FIG. 5 illustrates a cross section view of the catheter along line 5—5 of FIG. 1.

FIG. 5 illustrates a cross section view of the catheter 14 along line 5—5 of FIG. 1, where all numerals correspond to those elements previously described. Shown in particular is the semi-rigid intermediate tube 30 intimately engaging the proximal exhaust tube 28, the distal exhaust tube 32, and the proximal end 66 of the guidewire tube 46. A low profile mating of the distal end 36 of the proximal exhaust tube 28 with the semi-rigid intermediate tube 30 is accomplished by engagement of the distal end 36 of the proximal exhaust tube 28 with the reduced radius proximally located tubular portion 38 of the semi-rigid intermediate tube 30. Adhesives, welding, thermal bonding, heat shrinking, or other such suitable methods involving or not involving heat-generated bonding, can be incorporated to bond the distal end 36 of the proximal exhaust tube 28 with the reduced radius proximally located tubular portion 38 of the semi-rigid intermediate tube 30. The proximal end 66 of the guidewire tube 46 is accommodated by the truncated and rounded slot 68 of the semi-rigid intermediate tube 30 and secured thereto by an adhesive, by welding or other such suitable method. The proximal end 66 of the guidewire tube 46 is of such length that the outer profile of the distal exhaust tube 32 or the outer profile of the proximal exhaust tube 28 is not exceeded to maintain the desired minimal catheter profile. The portion of the truncated and rounded slot 68 which is not occupied by the proximal end 66 of the guidewire tube 46 and which is proximal thereto can also be utilized to accommodate a guidewire without structure interference. The proximal end 40 of the distal exhaust tube 32 intimately engages a portion of the distally located tubular portion 42 of the semi-rigid intermediate tube 30 and can be bonded thereto by an adhesive, welding, thermal bonding, heat shrinking, or other such suitable method involving or not involving heat-generated bonding. Also illustrated is the high pressure tube 48, having the lumen 78, passing through the lumens 50, 52 and 54. Lumen 50 of the proximal exhaust tube 28, lumen 52 of the semi-rigid intermediate tube 30, and lumen 54 of the distal exhaust tube 32 are connected to function as an exhaust route extending the length of the catheter 14.

Figure 6:
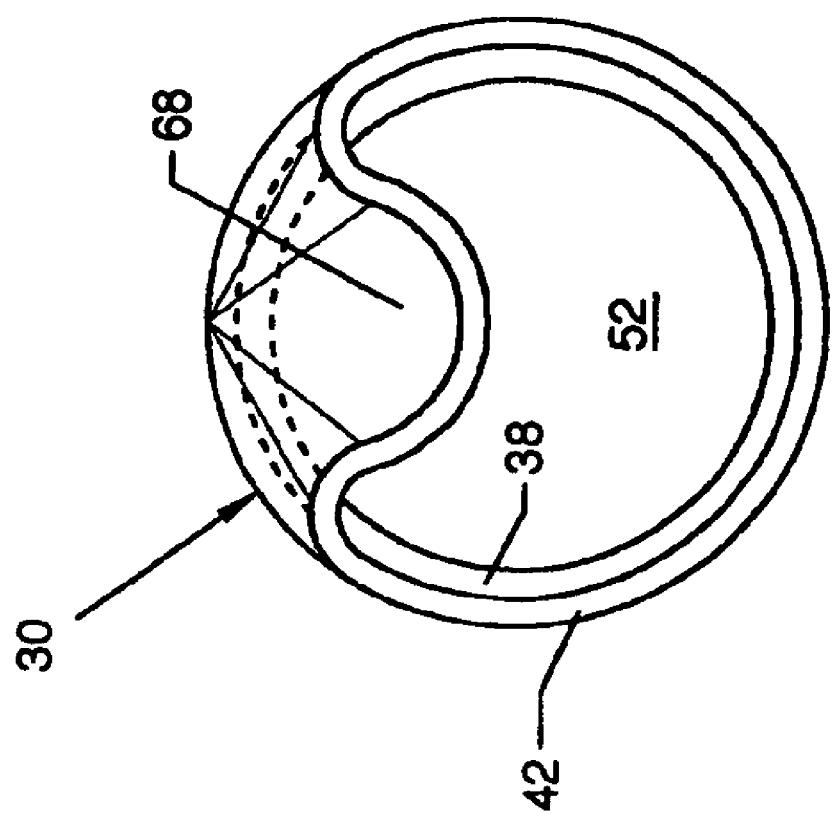
FIG. 6 illustrates an end view of the one-piece semi-rigid intermediate tube of FIG. 4.

FIG. 6 illustrates an end view of the one-piece semi-rigid intermediate tube 30 of FIG. 4, where all numerals correspond to those elements previously described. Illustrated in particular is the extreme distal end of the truncated and rounded slot 68 having a maximum arc.

Figure 7:
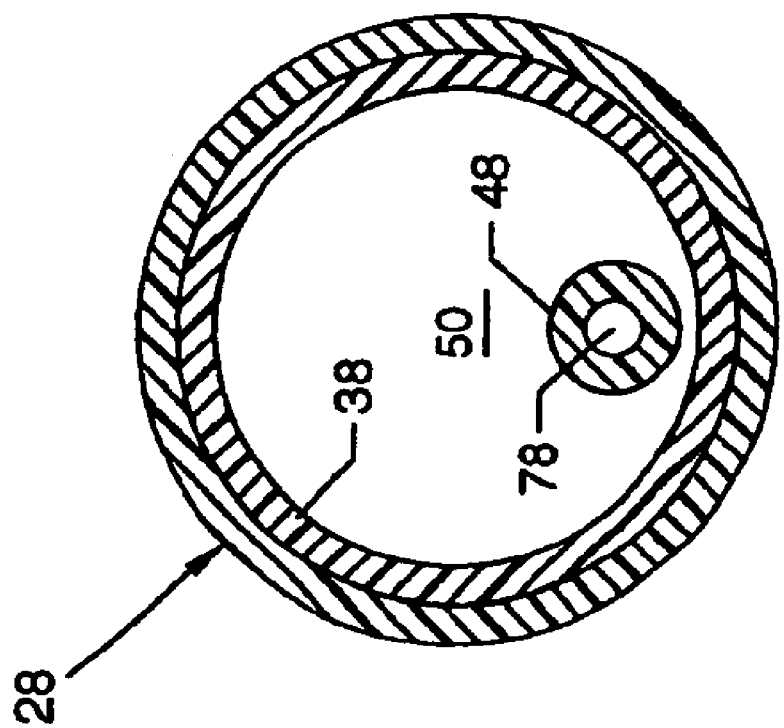
FIG. 7 illustrates a cross section of the catheter along line 7—7 of FIG. 5.

FIG. 7 illustrates a cross section of the catheter 14 along line 7—7 of FIG. 5, where all numerals correspond to those elements previously described. Illustrated in particular is the lumen 50 of the proximal exhaust tube 28 which functions as an exhaust route with minimal obstructions or restrictions therein.

Figure 8:
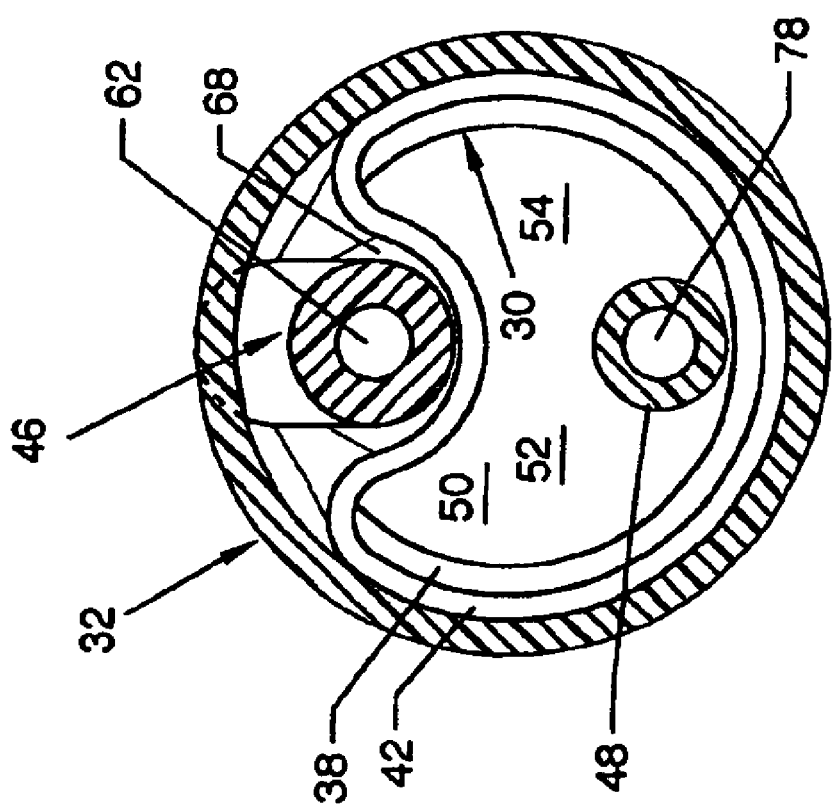
FIG. 8 illustrates a cross section of the catheter along line 8—8 of FIG. 5.

FIG. 8 illustrates a cross section of the catheter 14 along line 8—8 of FIG. 5, where all numerals correspond to those elements previously described. Illustrated in particular is the alignment and accommodation of the guidewire tube 46 in the truncated and rounded slot 68 of the semi-rigid intermediate tube 30. Also illustrated are the lumens 50, 52 and 54 in alignment to function as an exhaust route through the catheter 14.

Figure 9:
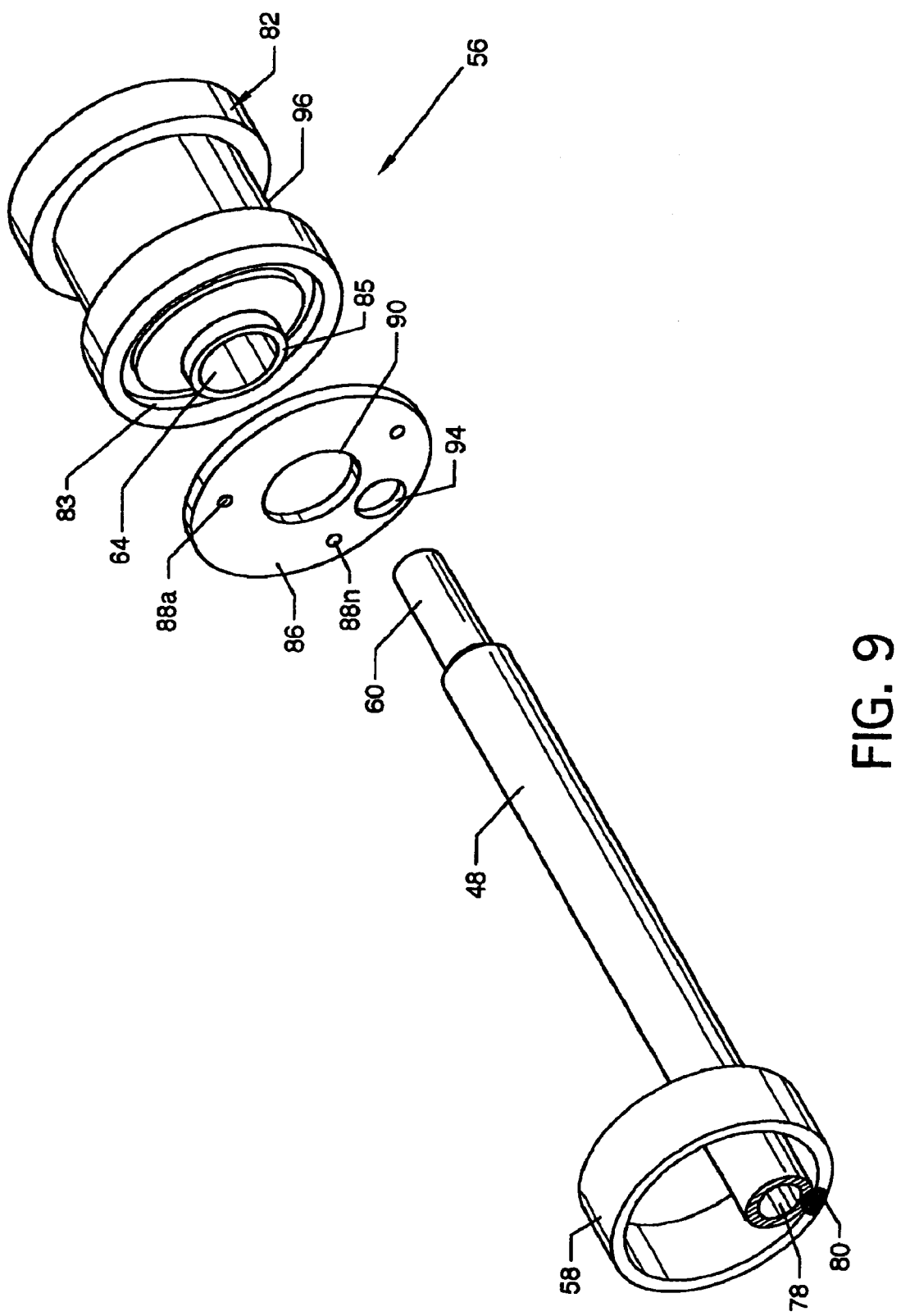
FIG. 9 illustrates an exploded isometric view depicting the fluid jet emanator, the exhaust tube support ring, and the high pressure tube in relationship to one another.

FIG. 9 illustrates an exploded isometric view depicting the fluid jet emanator 56, the exhaust tube support ring 58, and the high pressure tube 48 in relationship to one another. The exhaust tube support ring 58 secures such as by a weld 80 or other suitable attachment method to the lower surface of the high pressure tube 48 thereby fixing the exhaust tube support ring 58 at a suitable position along the interior (lumen 54) of the distal exhaust tube 32 for engagement with the distal exhaust tube 32 by compressional frictional engagement of the radiopaque marker band 72 over and about the distal exhaust tube 32.

Figure 10:
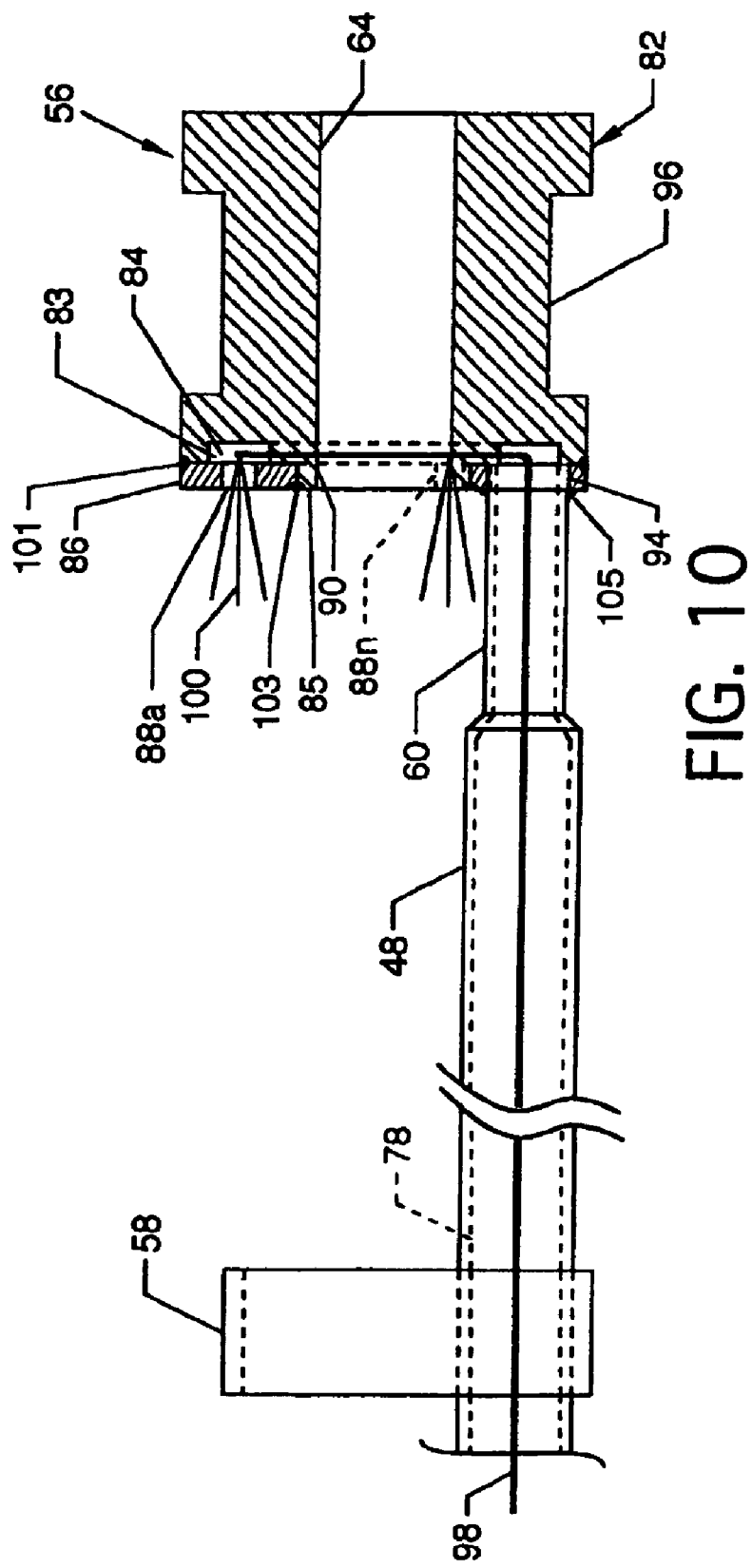
FIG. 10 illustrates a side view in partial cross section of the components illustrated in FIG. 9 in assembled condition.

The high pressure tube 48 is reduced in diameter at the high pressure tube distal end 60 to engage the fluid jet emanator 56. The fluid jet emanator 56 is described with reference to FIGS. 9, 10 and 11. The fluid jet emanator 56 is built as a structure outwardly resembling the general shape of a spool. The fluid jet emanator 56 includes a cylindrical main body 82, an annular manifold groove 83 in the form of a circular groove at the proximal end of the cylindrical main body 82, a centrally located tubular extension 85 extending proximally from the proximal end of the main body 82 and being coaxial with the annular manifold groove 83, and a manifold plate 86 aligned to the annular manifold groove 83 and to the planar annular surfaces adjacent to the annular manifold groove 83 and having a plurality of jet orifices 88a–88n, a centrally located hole 90, and an offset hole 94. The centrally located hole 90 is aligned to and accommodated by the tubular extension 85. The manifold plate 86 is also aligned substantially to the distal end of the main body 82 during the mating of the centrally located hole 90 and the tubular extension 85. A passageway 64 aligns to the longitudinal axis of the main body 82, the center of the tubular extension 85, the center of the hole 90 of the manifold plate 86, and the center of an annular groove 96 about the main body 82. As shown in FIG. 10, an annular manifold 84 is formed when the manifold plate 86 is mated over and about the annular manifold groove 83 and adjacent planar annular surfaces of the fluid jet emanator 56 at which time the plurality of jet orifices 88a–88n and the offset hole 94 are brought into close communicational alignment with the annular manifold groove 83 and annular manifold 84.

High pressure fluid 98 such as saline or other suitable solution is delivered through the lumen 78 of the high pressure tube 48 to the fluid jet emanator 56 and distributed through the annular manifold 84 to the plurality of jet orifices 88a–88n whereby high velocity jet flow 100 emanates proximally, as described later in detail.

The radiopaque marker band 70 and the annular groove 96 in the main body 82 of the fluid jet emanator 56 are utilized to fix the fluid jet emanator 56 and associated components and structures at the proper position within the distal end of the distal exhaust tube 32, as illustrated in FIG. 12. The radiopaque marker band 70 positions over and about the distal end of the distal exhaust tube 32 for engagement with the distal exhaust tube 32 by compressional frictional engagement of the radiopaque marker band 70 over and about distal exhaust tube 32 in the co-located region of the annular groove 96 and the distal exhaust tube 32.

FIG. 10 illustrates a side view in partial cross section of the components illustrated in FIG. 9 in assembled condition. Illustrated in particular is the connective relationship of the lumen 78 of the high pressure tube 48 to the annular manifold 84. High pressure fluid 98 is delivered to the annular manifold 84 through the lumen 78 and is emanated outwardly and proximally through the jet orifices 88a–88n in the form of high velocity jet flow 100 in multiple jet streams. Integrity of the annular manifold 84 is ensured by an annular weld 101 joining the common mated peripheries of the manifold plate 86 and adjacent main body 82 of the fluid jet emanator 56 and by another annular weld 103 joining the junction of the tubular extension 85 and the manifold plate 86. An annular weld 105 securingly seals the distal end 60 of the high pressure tube 48 within the offset hole 94, thereby ensuring the integrity of the connection of the lumen 78 with the annular manifold 84.

Figure 11:
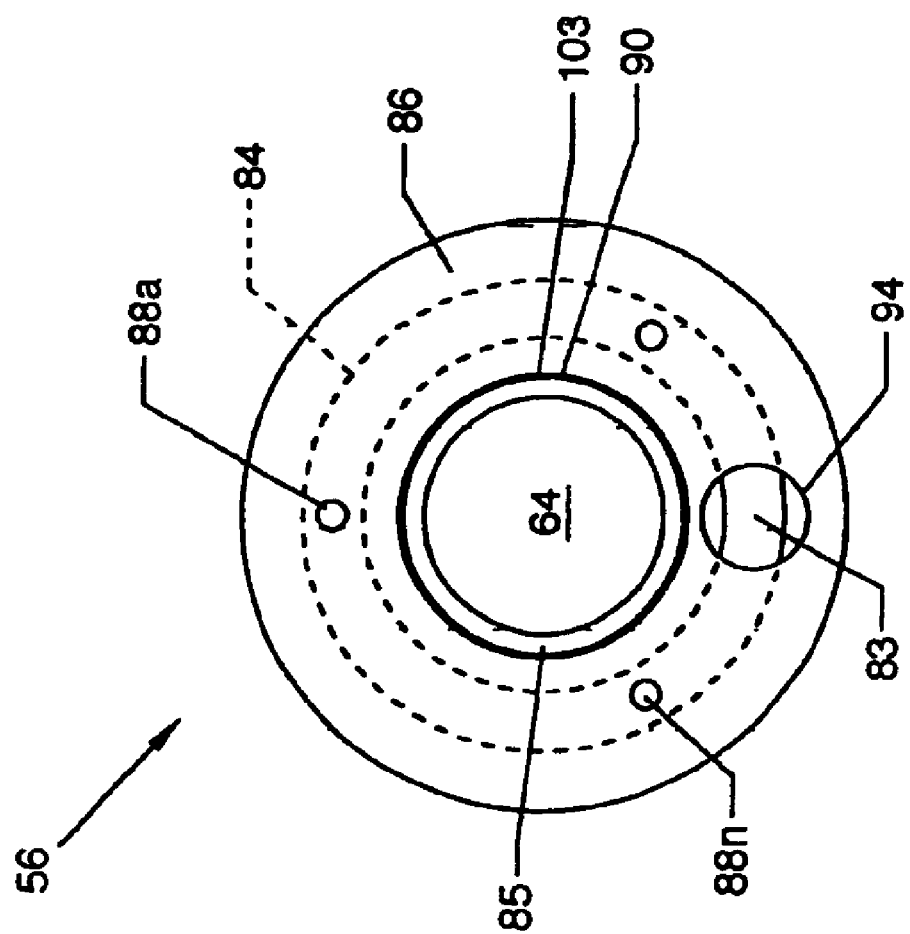
FIG. 11 illustrates a proximal end view of the fluid jet emanator.

FIG. 11 illustrates a proximal end view of the fluid jet emanator 56, where all numerals correspond to those elements previously described. Illustrated in particular is the distribution and alignment of the jet orifices 88a–88n about the annular manifold 84 through which high velocity jet flow 100 emanates proximally.

FIG. 12 illustrates a cross section view of the distal portion of the distal exhaust tube 32 along line 12—12 of FIG. 1. Shown in the illustration is the positioning of the radiopaque marker bands 70 and 72 around and about the distal portion of the distal exhaust tube 32. The distally located radiopaque marker band 70 is forcibly applied over and about the distal exhaust tube 32 to cause frictional annular engagement of a portion of the distal exhaust tube 32 with all or part of the annular groove 96 of the fluid jet emanator 56. Such frictional engagement is sufficient to place the outer radius surface of the radiopaque marker band 70 in a position lesser than the general and greater outer radial surface of the distal exhaust tube 32 thereby providing in part a distal exhaust tube 32 having no elements protruding beyond the general outer radial surface thereof for unimpeded and smooth distal or proximal transition of the catheter 14 within a vein, artery or the like. The frictional engagement of the radiopaque marker band 70 over and about the distal exhaust tube 32 is not abrupt in nature with respect to the smooth surface of the distal exhaust tube 32 wherein opposed curved annular surfaces 102 and 104 are formed adjacent to the edges of the radiopaque marker band 70. The curved annular surfaces 102 and 104 being generally smooth in nature also aid in unimpeded and smooth distal or proximal transition of the catheter 14 within a vein, artery or the like. The proximally located radiopaque marker band 72 is also forcibly applied over and about the distal exhaust tube 32 to cause frictional annular engagement of a portion of the distal exhaust tube 32 with the exhaust tube support ring 58 much in the same manner as the radiopaque marker band 70. Such frictional engagement is sufficient to place the outer radius surface of the radiopaque marker band 72 in a position lesser than the general and greater outer radial surface of the distal exhaust tube 32 thereby providing in part a distal exhaust tube 32 having no elements protruding beyond the general outer radial surface thereof for unimpeded and smooth distal or proximal transition of the catheter 14 within a vein, artery or the like. The curved annular surfaces 106 and 108 being generally smooth in nature also aid in unimpeded and smooth distal or proximal transition of the catheter 14.

Structure is provided to nurture and aid introduction of and passage of the distal portion of the distal exhaust tube 32 through blood vessels, arteries and the like to the site of thrombotic deposits or lesions. The tapered tip 44, as opposed to a rounded but nontapered tip, can part and can more easily penetrate thrombotic deposits or lesions during insertional travel in a distal direction instead of advancing or pushing such thrombotic deposits or lesions distally. The decreasing diameter in a distal direction of the tapered tip 44 also allows for increasing flexibility to negotiate and pass through tortuous paths. The portion of the distal exhaust tube 32 which immediately follows the tapered tip 44 on a tortuous negotiation and passage is influenced by supportive structure which offers reinforcement of the distal exhaust tube 32 against bending or collapsing due to negative pressures, especially in the regions in close proximity to or including the inflow orifices 76a–76n and the outflow orifices 74a–74n. The exhaust tube support ring 58 and the fluid jet emanator 56 are examples of structures offering support or reinforcement along the distal exhaust tube 32 in the regions of the inflow and outflow orifices 76a–76n and 74a–74n, respectively. The exhaust tube support ring 58 and the fluid jet emanator 56 also serve as forms and contribute to maintaining the diameter of the distal exhaust tube 32. Such support allows the use of thinner wall dimension for the distal tube 32 to allow for a larger and more effective and efficient sized lumen 54, as well as contributing to a lesser sized outer diameter. Such support also contributes to supportively maintaining the diameter and overall shape of the distal exhaust tube 32 when the catheter 14 is pushed or advanced along a vein or vessel, as well as providing torsional support.

MODE OF OPERATION

Figure 13:
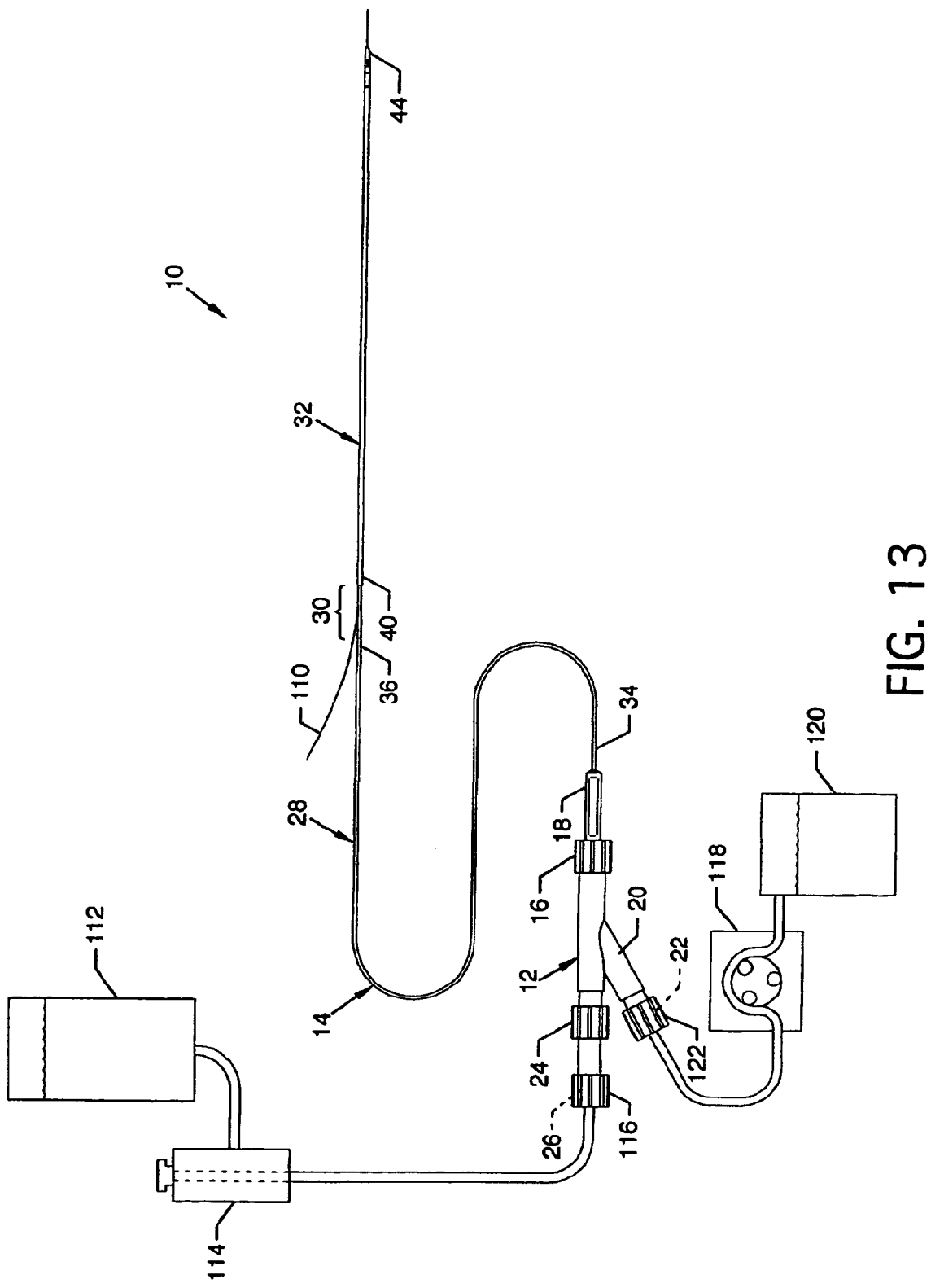
FIG. 13 illustrates the rapid exchange fluid jet thrombectomy device connected to ancillary devices.
Figure 14:
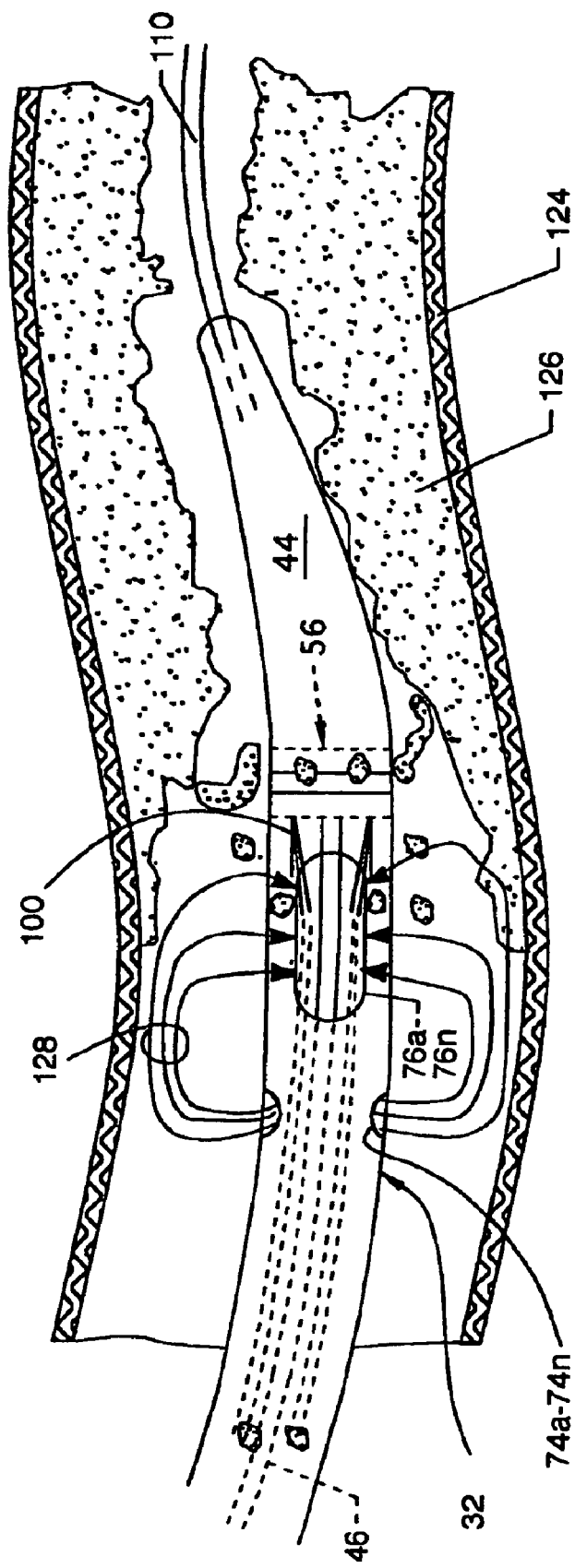
FIG. 14 illustrates a cross section view in partial cutaway of the rapid exchange fluid jet thrombectomy device in the performance of the method of use thereof.

FIGS. 13 and 14 illustrate the mode of operation where FIG. 13 illustrates the rapid exchange fluid jet thrombectomy device 10 connected to ancillary devices, and where FIG. 14 illustrates a cross section view in partial cutaway of the rapid exchange fluid jet thrombectomy device 10 in the performance of the method of use thereof. The mode of operation is best understood by referring to FIGS. 13 and 14, as well as previously described figures.

In FIG. 13, the rapid exchange fluid jet thrombectomy device 10 is shown engaged over and about a guidewire 110 where the guidewire 110 (previously engaged into a vein or artery) first engages the lumen 62 of the guidewire tube 46 at the tapered tip 44 of the distal exhaust tube 32 followed by exiting of the guidewire 110 from the lumen 62 at the proximal end 66 of the guidewire tube 46 at the semi-rigid intermediate tube 30. A high pressure fluid source 112 and a high pressure fluid pump 114 connect as shown to the manifold 12 via the threaded high pressure connection port 26 by a threaded nut 116 or optionally by a direct connection. An optional exhaust regulator 118 and a collection chamber 120 connect to the threaded branch end 22 of the exhaust branch 20 of the manifold 12 by a Luer fitting 122 as shown.

FIG. 14 illustrates a cross section view in partial cutaway of the rapid exchange fluid jet thrombectomy device 10 in the performance of the method of use thereof, with particular attention given to the distal portion of the distal exhaust tube 32 including the flexible tapered tip 44 positioned in a blood vessel 124, artery or the like at the site of a thrombotic deposit or lesion 126. Multiple jet streams of high velocity jet flow 100 of saline (or other suitable fluid) are shown being emitted in a proximal direction from the jet emanator 56 to impinge upon and carry away thrombotic deposits or lesions 126. Other jet emanators can be incorporated within the distal portion of the distal exhaust tube 32 as an alternative to the jet emanator 56 illustrated in this figure to emanate or emit one or more high velocity jet flow(s) 100 distally along or near the longitudinal axis of the distal exhaust tube 32 to accomplish the same purpose as that described for the jet emanator 56. The high velocity jet flow(s) 100 of saline pass outwardly through the outflow orifice(s) 74a–74n in a radial direction creating crossflow jet(s) 128 (lower velocity jet(s)) directed outwardly toward the wall of the blood vessel 124 and are influenced by the low pressure at the inflow orifice(s) 76a–76n to cause the crossflow jet(s) 128 to flow circumferentially and distally to impinge on, provide drag forces on, and break up thrombotic deposits or lesions 126 and to, by entrainment, urge and carry along the particles of thrombotic deposits or lesions 126 through the inflow orifice(s) 76a–76n, a relatively low pressure region, into the high velocity jet flows 100 where the thrombus is further macerated into microscopic particles, and into the distal exhaust tube lumen 54 (FIG. 12). A certain portion of this macerated debris which is mixed with fresh saline is removed through the exhaust tube lumen 54 and a certain portion flows back out the outflow orifices 74a–74n and recirculates to break up more debris which is returned to the inflow orifices 76a–76n. In this way, much more flow circulates through the system than is injected through the jet orifices 88a–88n. For purposes of illustration and example, three to ten times more flow circulates through the system than is delivered by the jet orifices 88a–88n. The entrainment through the inflow orifice(s) 76a–76n is based on entrainment by the high velocity jet flow(s) 100. The outflow is driven by internal pressure which is created by the high velocity jet flow(s) 100 and the fluid entrained through the inflow orifice(s) 76a–76n. Enhanced clot removal is attainable because of the recirculation pattern established between inflow and outflow orifices 76a–76n and 74a–74n, which creates a flow field that maximizes drag force on wall-adhered thrombus. Since the entrained thrombus is macerated into microscopic particles, those particles that exit the outflow orifices 74a–74n are not of sufficient size to significantly block the distal circulation, and will be re-entrained into the inflow orifices 76a–76n at a high rate. In a no flow situation or when flow is stopped with another device such as an occlusion balloon, then material can be recirculated and rediluted until all that remains is saline and all particles are removed.

Figure 15:
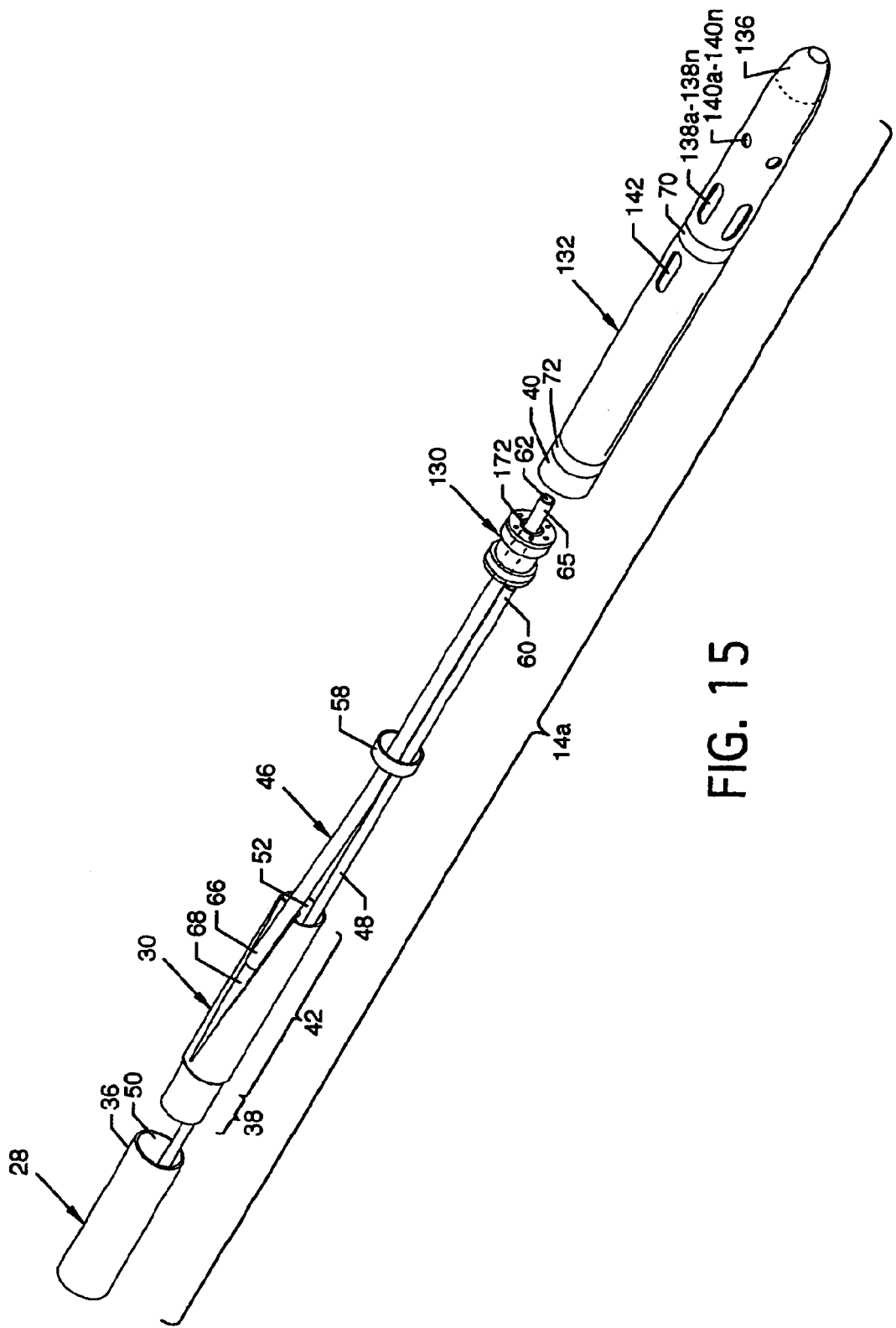
FIG. 15, an alternate embodiment, illustrates an exploded and foreshortened isometric view of the components of an alternative catheter, including a bi-directional fluid jet emanator, of the rapid exchange fluid jet thrombectomy device distal to the strain.

FIG. 15, an alternate embodiment, illustrates an exploded isometric view of the components of an alternate catheter 14a distal to the strain relief 18, the components being foreshortened with respect to length for the purpose of illustration and clarity. Many of the components utilized in the catheter 14a are the same as those utilized in the catheter 14 but some are different, and therefore the catheter 14 has been redesignated as catheter 14a. The fluid jet emanator 56 is redesignated as the bi-directional fluid jet emanator 130, and the distal exhaust tube 32 is redesignated as the distal exhaust tube 132. Other associated components may be utilized and may be relocated as shown herein. The outwardly visible length of the catheter 14a is comprised of outwardly visible joined components including the proximal exhaust tube 28, the semi-rigid intermediate tube 30, the distal exhaust tube 132, and a small portion of the guidewire tube 46. Other components or structures are housed within, around and about the catheter 14a.

Figure 18:
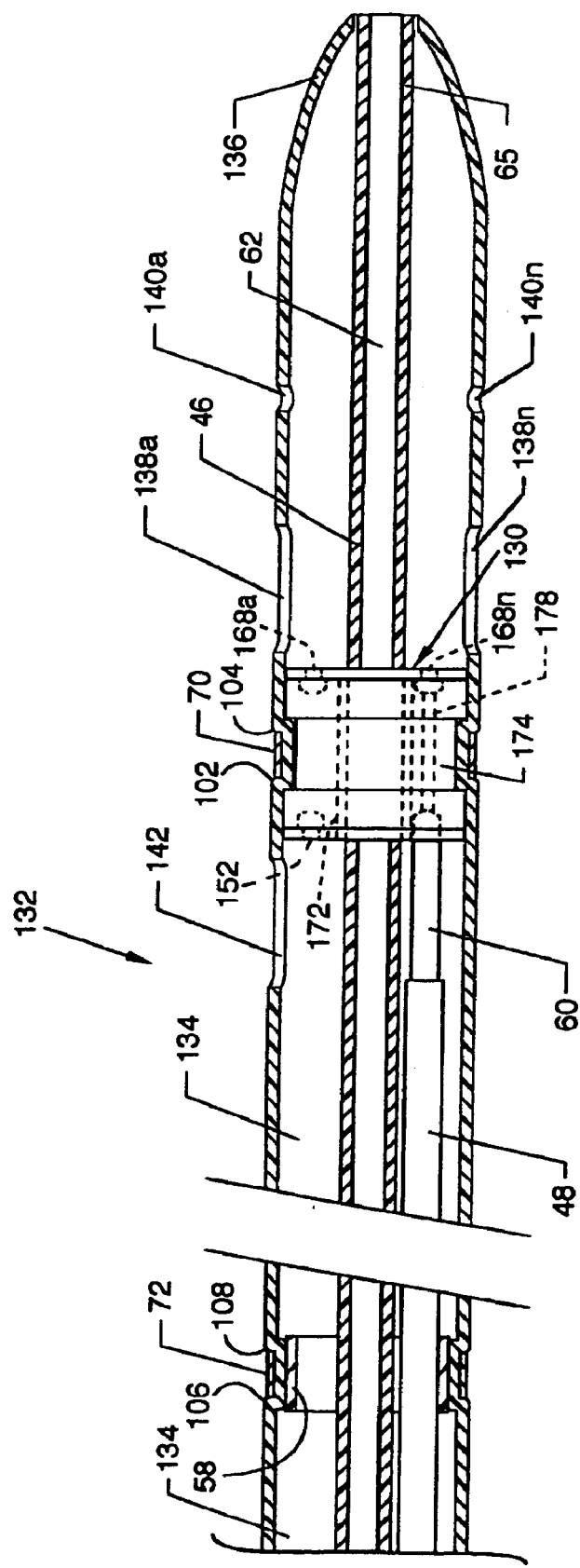
FIG. 18 illustrates a cross sectional view of the distal portion of the distal exhaust tube of the alternate embodiment; and, FIG. 19 illustrates a cross section view in partial cutaway of the rapid exchange fluid jet thrombectomy device incorporating the bi-directional fluid jet emanator in the performance of the method of use thereof.

The high pressure tube 48 with a lumen 78 (FIG. 5) extends from the manifold 12, as previously described, through the lumen 50 in the proximal exhaust tube 28, through the lumen 52 in the semi-rigid intermediate tube 30, and through a lumen 134 (FIG. 18) of the distal exhaust tube 132 and connectively terminates at the bi-directional fluid jet emanator 130. The high pressure tube 48 also extends through and is attached to the exhaust tube support ring 58 such as by welding or other suitable means. The bi-directional fluid jet emanator 130 as well as the distal end 60 of the high pressure tube 48 locate distally in the lumen 134 of the distal exhaust tube 132, as shown in FIG. 18. A radiopaque marker band 70 aligns over and about the distal region of the distal exhaust tube 132 and is forcibly secured thereto in captured alignment and in transmitted frictional engagement with the bi-directional fluid jet emanator 130, as shown in FIG. 18. The exhaust tube support ring 58 locates in lumen 134 of the distal exhaust tube 132 in alignment with a radiopaque marker band 72 which forcibly secures over and about the distal exhaust tube 132 in transmitted frictional engagement, as shown in FIG. 18. The guidewire tube 46, having the lumen 62, extends distally from the semi-rigid intermediate tube 30, through the exhaust tube support ring 58, into the lumen 134 of the distal exhaust tube 132, as shown in FIG. 18, through a passageway 172 in the bi-directional fluid jet emanator 130, and continues through the lumen 134 of the distal exhaust tube 132 where the distal end 65 terminates securely at the distal end of the tip 136. The proximal end 66 of the guidewire tube 46 is securely accommodated by the truncated and rounded slot 68 of the semi-rigid intermediate tube 30 described with reference to FIG. 4. A plurality of inflow orifices are located along and about the distal region of the distal exhaust tube 132, including inflow orifices 138a–138n in distally near juxtaposition to the radiopaque marker band 70 and the bi-directional fluid jet emanator 130 (FIG. 18); and a plurality of outflow orifices 140a–140n are located along and about the distal region of the distal exhaust tube 132 distally from the radiopaque marker band 70 and the bi-directional fluid jet emanator 130, as also shown in FIG. 18. In addition, an inflow orifice 142 is located in proximally near juxtaposition to the radiopaque marker band 70, as also shown in FIG. 18.

Figure 16:
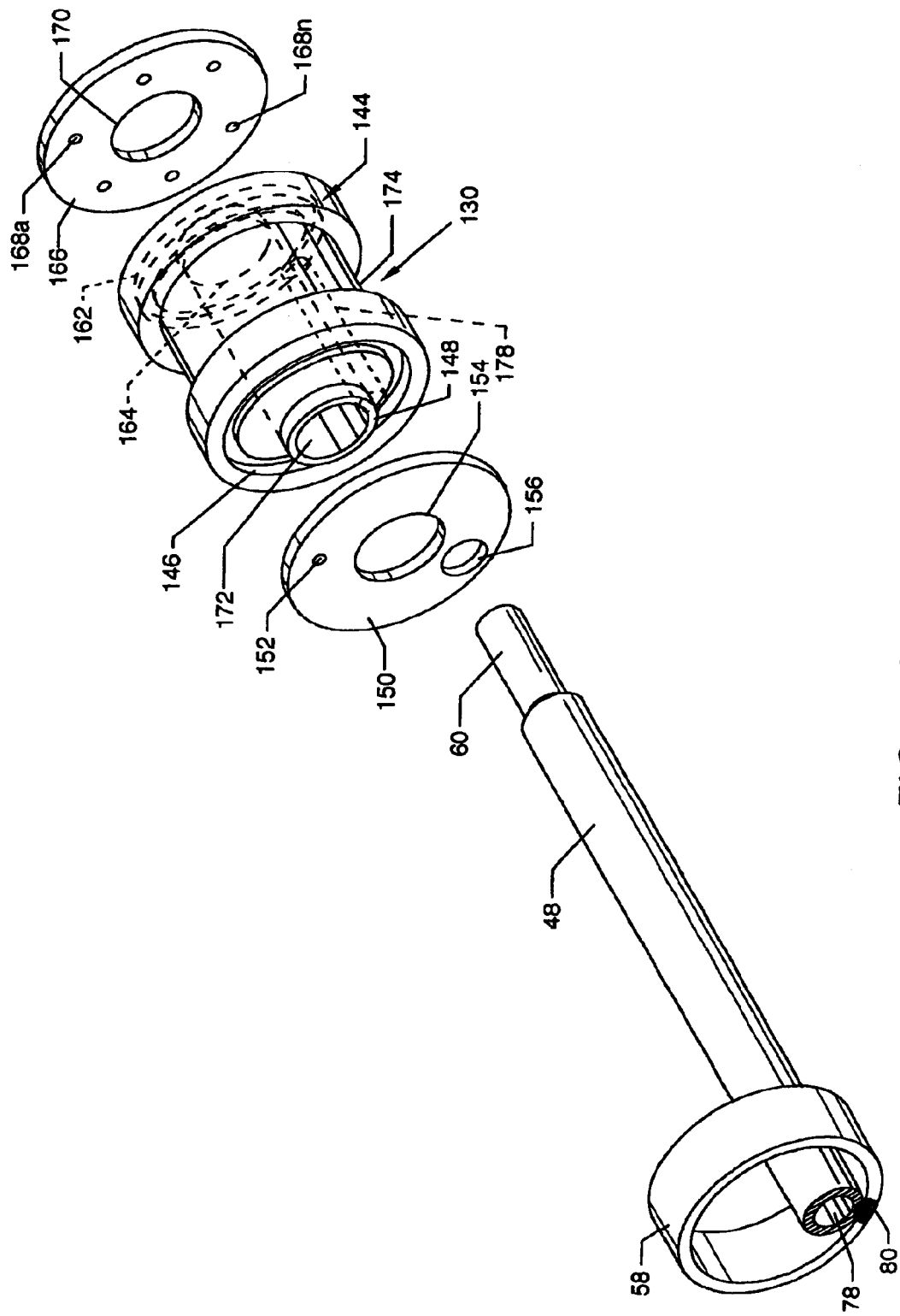
FIG. 16 illustrates an exploded isometric view depicting the bi-directional fluid jet emanator, the exhaust tube support ring, and the high pressure tube in relationship to one another.

FIG. 16 illustrates an exploded isometric view depicting the bi-directional fluid jet emanator 130, the exhaust tube support ring 58, and the high pressure tube 48 in relationship to one another. The exhaust tube support ring 58 secures such as by a weld 80 or other suitable attachment method to the lower surface of the high pressure tube 48 thereby fixing the exhaust tube support ring 58 at a suitable position along the interior (lumen 134) of the distal exhaust tube 132 for engagement with the distal exhaust tube 132 by compressional frictional engagement of the radiopaque marker band 72 over and about the distal exhaust tube 132.

Figure 17:
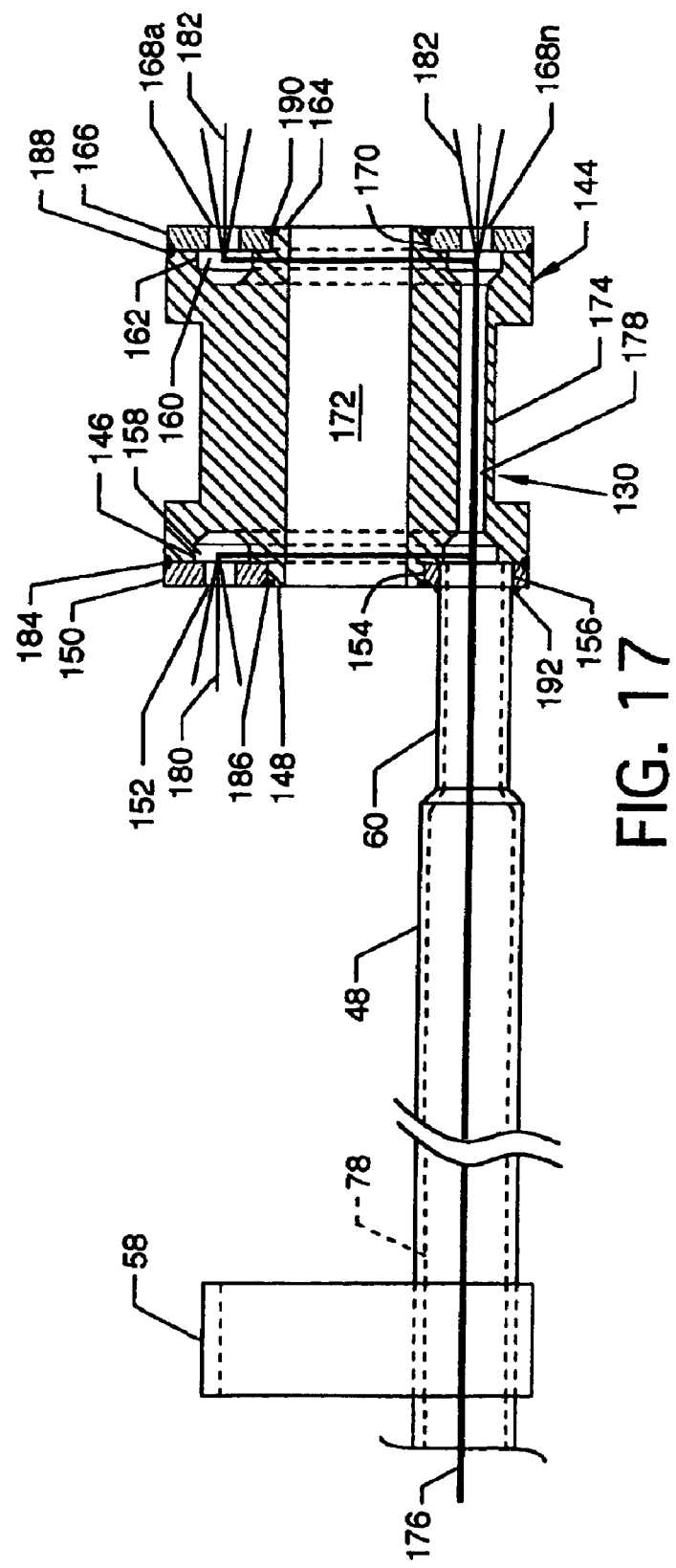
FIG. 17 illustrates a side view in partial cross section of the components illustrated in FIG. 16 in assembled condition.

The high pressure tube 48 is reduced in diameter at the high pressure tube distal end 60 to engage the bi-directional fluid jet emanator 130. The bi-directional fluid jet emanator 130, being similar in many aspects to the fluid jet emanator 56, is described with reference to FIGS. 16 and 17. The bi-directional fluid jet emanator 130 is built as a structure outwardly resembling the general shape of a spool. The bi-directional fluid jet emanator 130 includes a cylindrical main body 144, an annular manifold groove 146 in the form of a circular groove at the proximal end of the cylindrical main body 144, a centrally located tubular extension 148 extending proximally from the proximal end of the main body 144 and being coaxial with the annular manifold groove 146, and a manifold plate 150 aligned to the annular manifold groove 146 and to the planar annular surfaces adjacent to the annular manifold groove 146 and having a jet orifice 152, a centrally located hole 154, and an offset hole 156. The centrally located hole 154 is aligned to and accommodated by the tubular extension 148. The manifold plate 150 is also aligned substantially to the distal end of the main body 144 during the mating of the centrally located hole 154 and the tubular extension 148. As shown in FIG. 17, an annular manifold 158 is formed when the manifold plate 150 is mated over and about the annular manifold groove 146 and adjacent planar annular surfaces of the bi-directional fluid jet emanator 130 at which instance the jet orifice 152 and the offset hole 156 are brought into close communicational alignment with the annular manifold groove 146 and annular manifold 158. The bi-directional fluid jet emanator 130 also includes another annular manifold 160 (FIG. 17) opposite the annular manifold 158 which is formed in a like and similar fashion to the annular manifold 158 and which is located at the distal end of the bi-directional fluid jet emanator 130.

With reference to FIGS. 16 and 17, the annular manifold 160 and other structure at the distal end of the bi-directional fluid jet emanator 130 is now described. The distal end of the bi-directional fluid jet emanator 130 includes an annular manifold groove 162 in the form of a circular groove at the distal end of the cylindrical main body 144, a centrally located tubular extension 164 extending distally from the distal end of the main body 144 and being coaxial with the annular manifold groove 162, and a manifold plate 166 aligned to the annular manifold groove 162 and the planar annular surfaces adjacent to the annular manifold groove 162 and having a plurality of jet orifices 168a–168n distributed about the manifold plate 166, and a centrally located hole 170. The centrally located hole 170 is aligned to and accommodated by the tubular extension 164. The manifold plate 166 is also aligned substantially to the distal end of the main body 144 during the mating of the centrally located hole 170 and the tubular extension 164. The annular manifold 160 is formed when the manifold plate 166 is mated over and about the annular manifold groove 162 and adjacent planar annular surfaces of the bi-directional fluid jet emanator 130 at which instance the jet orifices 168a–168n and the hole 170 are brought into close communicational alignment with the annular manifold groove 162 and annular manifold 160. A passageway 172 aligns to the longitudinal axis of the main body 144, the centers of the holes 154 and 170 of the manifold plates 150 and 166, and the center of an annular groove 174 about the main body 144. An additional passageway 178 communicatingly extends through the main body 144 between the proximally located annular manifold 158 and the distally located annular manifold 160.

The radiopaque marker band 70 and the annular groove 174 located about the main body 144 of the bi-directional fluid jet emanator 130 are utilized to fix the bi-directional fluid jet emanator 130 and associated components and structures at the proper position within the distal end of the distal exhaust tube 132, as illustrated in FIG. 18. The radiopaque marker band 70 positions over and about the distal end of the distal exhaust tube 132 for engagement with the distal exhaust tube 132 by compressional frictional engagement of the radiopaque marker band 70 over and about distal exhaust tube 132 in the co-located region of the annular groove 174 and the distal exhaust tube 132.

FIG. 17 illustrates a side view in partial cross section of the assembled components illustrated in FIG. 16 in assembled condition. Illustrated in particular is the connective relationship of the lumen 78 of the high pressure tube 48 to the annular manifold 158, to the passageway 178, and to the annular manifold 160. High pressure fluid 176 delivered to the annular manifold 158 through the lumen 78 is emanated outwardly and proximally through the jet orifice 152 in the form of high velocity jet flow 180 in a jet stream. High pressure fluid 176 delivered to the annular manifold 158 through the lumen 78 communicates with annular manifold 160 via the interconnecting passageway 178 and is emanated outwardly and distally through the jet orifices 168a–168n in the form of high velocity jet flow 182 in jet streams. Integrity of the annular manifold 158 is ensured by an annular weld 184 joining the common mated peripheries of the manifold plate 150 and adjacent main body 144 of the bi-directional fluid jet emanator 130 and by another annular weld 186 joining the junction of the tubular extension 148 and the manifold plate 150. In a similar fashion, integrity of the annular manifold 160 is ensured by an annular weld 188 joining the common mated peripheries of the manifold plate 166 and adjacent main body 144 of the bi-directional fluid jet emanator 130 and by another annular weld 190 joining the junction of the tubular extension 164 and the manifold plate 166. An annular weld 192 securingly seals the distal end 60 of the high pressure tube 48 within the offset hole 156, thereby ensuring the integrity of the connection of the lumen 78 with the annular manifold 158.

FIG. 18 illustrates a cross section view of the distal portion of the distal exhaust tube 132 in a fashion such as incorporated along line 12—12 of FIG. 1 showing the relationship of the bi-directional fluid jet emanator 130 to the distally located inflow orifices 138a–138n and outflow orifices 140a–140n and to the proximally located inflow orifice 142. Shown in the illustration is the positioning of the radiopaque marker bands 70 and 72 around and about the distal portion of the distal exhaust tube 132 which also form curved annular surfaces 102, 104, 106 and 108, as previously described. The distally located radiopaque marker band 70 is forcibly applied over and about the distal exhaust tube 132 to cause frictional annular engagement of a portion of the distal exhaust tube 132 with all or part of the annular groove 174 of the bi-directional fluid jet emanator 130. Such frictional engagement is sufficient to place the outer radius surface of the radiopaque marker band 70 in a position lesser than, the general and greater outer radial surface of the distal exhaust tube 132, thereby providing, in part, a distal exhaust tube 132 having no elements protruding beyond the general outer radial surface thereof for unimpeded and smooth distal or proximal transition of the catheter 14a within a vein, artery or the like in a manner and fashion such as previously described.

MODE OF OPERATION

Figure 19:
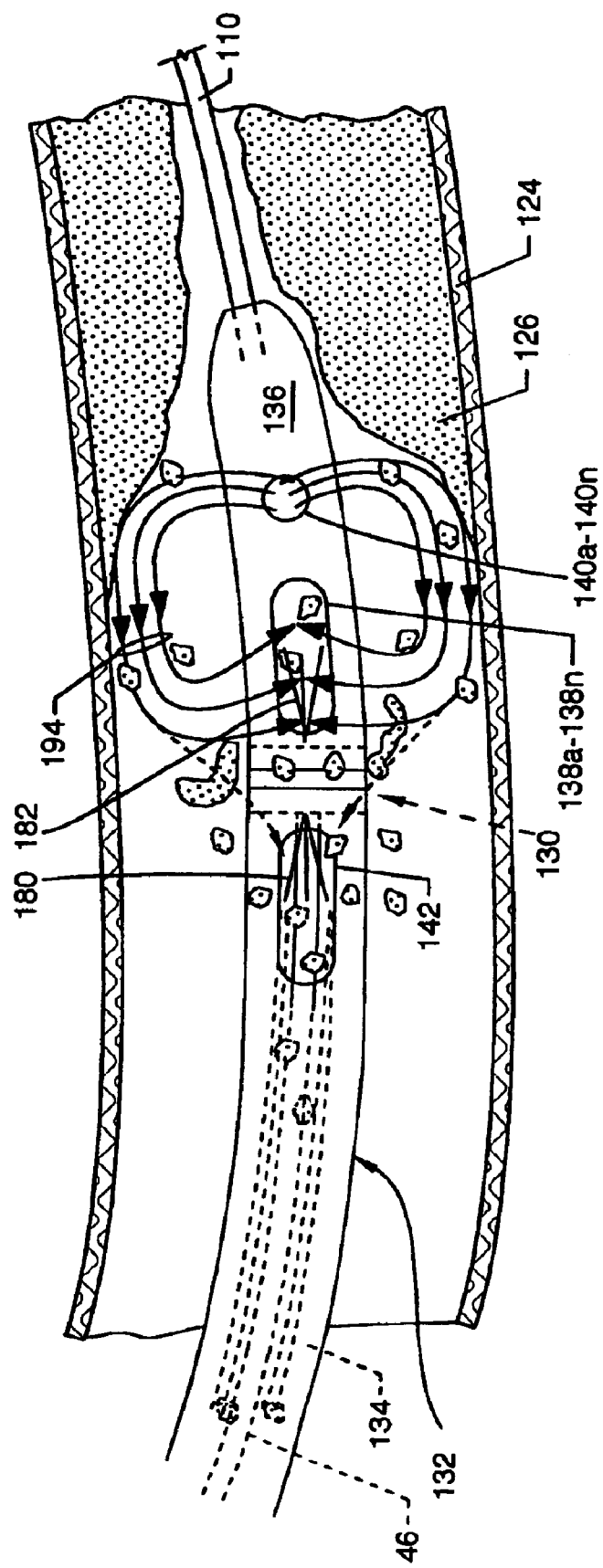

The mode of operation of the rapid exchange fluid jet thrombectomy device 10 incorporating the catheter 14a including the bi-directional fluid jet emanator 130 and the alternative distal exhaust tube 132 and associated components and structures is best understood by referring particularly to FIG. 19 which illustrates a cross section view in partial cutaway of the distal region of the catheter 14a of the rapid exchange fluid jet thrombectomy device 10 in the performance of the method of use thereof. The distal exhaust tube 132 is configured and connected in a manner and fashion such as described in relation to FIG. 3 but where the distal exhaust tube 132 is substituted for the distal exhaust tube 32.

FIG. 19 shows in particular the distal portion of the distal exhaust tube 132 including the tip 136 positioned in a blood vessel 124, artery or the like at the site of a thrombotic deposit or lesion 126. High velocity jet flow occurs in opposing directions from the bi-directional fluid jet emanator 130. High velocity jet flow 182 emanating distally from the bi-directional fluid jet emanator 130 serves to provide for breaking up and macerating or re-macerating of thrombotic deposits or lesions 126, and high velocity jet flow 180 emanating proximally from the bi-directional fluid jet emanator 130 serves to provide for removal of macerated or re-macerated thrombotic deposits or lesions 126 through the lumen 134 of the distal exhaust tube 132.

With respect to distally directed jet streams, multiple jet streams of high velocity jet flow 182 of saline (or other suitable fluid), such as also viewed in FIG. 17, are shown being emanated in a distal direction from the bi-directional fluid jet emanator 130 to impinge upon and carry away thrombotic deposits or lesions 126. The high velocity jet flow(s) 182 of saline pass outwardly through the outflow orifice(s) 140a–140n in a radial direction creating crossflow jet(s) 194 (lower velocity jet(s)) directed outwardly toward the wall of the blood vessel 124 and are influenced by the low pressure at the inflow orifice(s) 138a–138n to cause the crossflow jet(s) 194 to flow circumferentially and proximally to impinge on, provide drag forces on, and break up thrombotic deposits or lesions 126 and to, by entrainment, urge and carry along the particles of thrombotic deposits or lesions 126 through the inflow orifice(s) 138a–138n, a relatively low pressure region, and thence into the high velocity jet flows 182 once again where the thrombus is further macerated into microscopic particles. A certain portion of this macerated debris which is mixed with fresh saline is removed through the inflow orifice 142, as later described, through the distal exhaust tube lumen 134, and a certain portion flows into the inflow orifices 138a–138n and back out the outflow orifices 140a–140n and recirculates to break up more debris which is returned to the inflow orifices 138a–138n. In this way, much more flow circulates through the system than is injected through the jet orifices 168a–168n. For purposes of illustration and example, three to ten times more flow circulates through the system than is delivered by the jet orifices 168*a*–168*n*. The entrainment through the inflow orifice(s) 138*a*–138*n* is based on entrainment by the high velocity jet flow(s) 182. Enhanced clot removal is attainable because of the recirculation pattern established between inflow and outflow orifices 138*a*–138*n* and 140*a*–140*n*, which creates a flow field that maximizes drag force on wall-adhered thrombus. Since the entrained thrombus is macerated into microscopic particles, those particles that exit the outflow orifices 140*a*–140*n* are not of sufficient size to significantly block the distal circulation, and will be re-entrained into the inflow orifices 138*a*–138*n* at a high rate or exhausted through the inflow orifice 142.

With respect to the proximally directed jet stream, a jet stream of high velocity jet flow 180 of saline (or other suitable fluid), such as also viewed in FIG. 17, is shown being emitted in a proximal direction from the bi-directional fluid jet emanator 130 by the proximally facing jet orifice 152 to create a relatively low pressure at the inflow orifice 142 to induct and carry away macerated or re-macerated thrombotic deposits or lesions 126 suspended in saline fluid. Although only one jet orifice 152 is shown in the preceding illustrations, one or more proximally facing orifices could be incorporated. The macerated or re-macerated thrombotic deposits or lesions 126 suspended in saline fluid are carried through the lumen 134 of the distal exhaust tube 132 to be collected as previously described.

In a no flow situation or when flow is stopped with another device such as an occlusion balloon, then material can be recirculated and rediluted until all that remains is saline and all particles are removed.

Various modifications can be made to the ion without departing from the apparent scope hereof.

It is claimed:

RAPID EXCHANGE FLUID JET THROMBECTOMY DEVICE AND METHOD PARTS LIST

| | |
|---|---|
| 10 | rapid exchange fluid jet thrombectomy device |
| 12 | manifold |
| 14 | catheter |
| 14a | catheter |
| 16 | Luer fitting |
| 18 | strain relief |
| 20 | exhaust branch |
| 22 | threaded branch end |
| 24 | Luer fitting |
| 26 | threaded high pressure connection port |
| 28 | proximal exhaust tube |
| 30 | semi-rigid intermediate tube |
| 32 | distal exhaust tube |
| 34 | proximal end (of proximal exhaust tube) |
| 36 | distal end (of proximal exhaust tube) |
| 38 | proximally located tubular portion (of semi-rigid intermediate tube) |
| 40 | proximal end (of distal exhaust tube) |
| 42 | distally located tubular portion (of semi-rigid intermediate tube) |
| 44 | tapered tip |
| 46 | guidewire tube |
| 48 | high pressure tube |
| 50 | lumen (of proximal exhaust tube) |
| 52 | lumen (of semi-rigid intermediate tube) |
| 54 | lumen (of distal exhaust tube) |
| 56 | fluid jet emanator |
| 58 | exhaust tube support ring |
| 60 | distal end (of high pressure tube) |
| 62 | lumen (of guidewire tube) |
| 64 | passageway |
| 65 | distal end (of guidewire tube) |
| 66 | proximal end (of guidewire tube) |
| 68 | truncated and rounded slot |
| 70 | radiopaque marker band |
| 72 | radiopaque marker band |
| 74a-n | outflow orifices |
| 76a-n | inflow orifices |
| 78 | lumen (of high pressure tube) |
| 80 | weld |
| 82 | main body |
| 83 | annular manifold groove |
| 84 | annular manifold |
| 85 | tubular extension |
| 86 | manifold plate |
| 88a-n | jet orifices |
| 90 | hole |
| 94 | offset hole |
| 96 | annular groove |
| 98 | high pressure fluid |
| 100 | high velocity jet flow |
| 101 | annular weld |
| 102 | curved annular surface |
| 103 | annular weld |
| 104 | curved annular surface |
| 105 | annular weld |
| 106 | curved annular surface |
| 108 | curved annular surface |
| 110 | guidewire |
| 112 | high pressure fluid source |
| 114 | high pressure fluid pump |
| 116 | threaded nut |
| 118 | exhaust regulator |
| 120 | collection chamber |
| 122 | Luer fitting |
| 124 | blood vessel |
| 126 | thrombotic deposit or lesion |

RAPID EXCHANGE FLUID JET THROMBECTOMY DEVICE AND METHOD PARTS LIST

| | |
|---|---|
| 128 | crossflow jets |
| 130 | bi-directional fluid jet emanator |
| 132 | distal exhaust tube |
| 134 | lumen |
| 136 | tip |
| 138a-n | inflow orifices |
| 140a-n | outflow orifices |
| 142 | inflow orifice |
| 144 | main body |
| 146 | annular manifold groove |
| 148 | tubular extension |
| 150 | manifold plate |
| 152 | jet orifice |
| 154 | hole |
| 156 | offset hole |
| 158 | annular manifold |
| 160 | annular manifold |
| 162 | annular manifold groove |
| 164 | tubular extension |
| 166 | manifold plate |
| 168a-n | jet orifices |
| 170 | hole |
| 172 | passageway |
| 174 | annular groove |
| 176 | high pressure fluid |
| 178 | passageway |
| 180 | high velocity jet flow |
| 182 | high velocity jet flow |
| 184 | weld |
| 186 | weld |
| 188 | weld |
| 190 | weld |
| 192 | weld |
| 194 | crossflow jets |

1. A rapid exchange fluid jet device for breaking apart tissue or other material in a biological or synthetic body vessel or cavity comprising:
   a. a unitary elongated structure with a proximal end and a distal end and defining a length between said proximal end and said distal end;
   b. said unitary elongated structure having tubular means extending along the length thereof, said tubular means defining at least a first passage for carrying a flow of high pressure fluid from said proximal end of said unitary elongated structure to said distal end of said unitary elongated structure, said first passage having a proximal end and a distal end, and high pressure connection means for supplying high pressure fluid to said proximal end of said first passage;
   c. a distal exhaust tube extending a portion of the length of said unitary elongated structure, said distal exhaust tube having a proximal end and a distal end, said distal exhaust tube being located in the region near said distal end of said unitary elongated structure, said distal exhaust tube having at least one inflow orifice and at least one outflow orifice;
   d. a proximal exhaust tube extending a portion of the length of said unitary elongated structure, said proximal exhaust tube having a proximal end and a distal end, said proximal exhaust tube being located in the region near said proximal end of said unitary elongated structure, and exhaust connection means communicating with said proximal end of said proximal exhaust tube;
   e. a guidewire tube extending from a location near the proximal end of said distal exhaust tube to a location near the distal end of said distal exhaust tube, said guidewire tube providing for passage of a guidewire from a point outside said unitary elongated structure near said proximal end of said distal exhaust tube to the distal end of said distal exhaust tube through said guidewire tube;
   f. a semi-rigid intermediate tube providing fluid communication between said proximal end of said distal exhaust tube and said distal end of said proximal exhaust tube, said semi-rigid intermediate tube having a truncated and rounded slot, said truncated and rounded slot fitting said guidewire tube near said proximal end of said distal exhaust tube;
   g. a jet emanator in fluid communication with said first passage, said jet emanator having at least one jet orifice, said at least one jet orifice forming high velocity fluid jet(s) by passage of high pressure fluid through said orifice(s); at least one of said jet orifice(s) directing at least one of said fluid jet(s) towards said distal exhaust tube and entraining surrounding blood or other fluid from the body vessel through said inflow orifice(s) into said distal exhaust tube creating a region of elevated pressure therein;
   h. said outflow orifice(s) creating cross stream jet(s) by passage of blood or other fluid and debris through said outflow orifice(s); and,
   i. said distal exhaust tube, said semi-rigid intermediate tube, and said proximal exhaust tube providing fluid passage for transporting thrombus or other unwanted tissue or debris from the distal end of said unitary elongated structure to the proximal end of said unitary elongated structure.

2. The device of claim 1, further comprising position indicator means for indicating the position of said distal exhaust tube.

3. The device of claim 2, wherein said position indicator means comprises at least one radiopaque marker band.

4. The device of claim 1, further comprising a flexible tip assembly fixed to said distal end of said distal exhaust tube.

5. The device of claim 1, wherein said outflow orifice(s) are located proximally of said inflow orifice(s).

6. The device of claim 1, wherein said jet emanator comprises a tip assembly with at least one passage communicating with said distal end of said first passage, and with at least one jet orifice communicating with said at least one passage.

7. The device of claim 1, further comprising exhaust regulation means for regulation of the rate of removal of fluid and thrombus or other unwanted material debris from the body vessel or cavity along said proximal exhaust tube.

8. A rapid exchange fluid jet device for breaking apart tissue or other material in a biological or synthetic body vessel or cavity comprising:
   a. a high pressure supply tube;
   b. a jet emanator;
   a distal exhaust tube;
   a proximal exhaust tube, said proximal exhaust tube being longer than said distal exhaust tube;
   e. a semi-rigid intermediate tube, said semi-rigid intermediate tube having a size and a shape enabling passage within a body vessel; and,
   f. a guidewire tube.

9. The device of claim 8, further comprising position indicator means for indicating the position of said distal exhaust tube.

10. The device of claim 8, wherein said jet emanator directs at least one fluid jet into said distal exhaust tube.

11. The device of claim 8, wherein said jet emanator directs at least one fluid jet in a proximal direction towards said distal exhaust tube.

12. A rapid exchange fluid jet system comprising:
   a. a rapid exchange catheter having a high pressure supply tube, a proximal high pressure supply connector, a jet emanator, a distal exhaust tube, a proximal exhaust tube longer than the distal exhaust tube, a proximal exhaust connector, a semi-rigid intermediate tube, a guidewire, the semi-rigid intermediate tube being sized and shaped for passage in a body vessel and providing connection for the distal exhaust tube and the proximal exhaust tube and the guidewire tube;
   b. a guidewire;
   c. a high pressure fluid source connected to said proximal high pressure supply connector; and,
   d. exhaust collection means connected to said proximal exhaust connector.

13. The system of claim 12, further comprising at least one orifice in said jet emanator, said at least one orifice directing at least one fluid jet towards said distal exhaust tube creating stagnation pressure which aids in driving a flow of blood or other fluid and unwanted material along said distal exhaust tube.

14. The system of claim 13, further comprising exhaust regulation means for regulating the rate of flow of blood or other fluid and unwanted material flowing into said exhaust collection means.

15. A rapid exchange fluid jet system comprising:
   a. a rapid exchange catheter having a high pressure supply tube, a proximal high pressure supply connector, a jet emanator, a distal exhaust tube, a proximal exhaust tube, a proximal exhaust connector, a semi-rigid intermediate tube, a guidewire tube;
   b. a guidewire;
   c. a high pressure fluid source connected to said proximal high pressure supply connector;
   d. exhaust collection means connected to said proximal exhaust connector;
   e. at least one inflow orifice and at least one outflow orifice in said distal exhaust tube;
   f. at least one orifice in said jet emanator, said at least one orifice directing at least one fluid jet towards said distal exhaust tube for entraining surrounding blood or other fluid through said inflow orifice(s) into said distal exhaust tube to thereby create a region of elevated pressure therein; and,
   g. said outflow orifice(s) creating cross stream jet(s) by passage of blood or other fluid and debris through said outflow orifice(s).

* * * * *